(12) United States Patent
Huang et al.

(10) Patent No.: US 10,485,423 B2
(45) Date of Patent: Nov. 26, 2019

(54) QUANTIFICATION OF LOCAL CIRCULATION WITH OCT ANGIOGRAPHY

(71) Applicant: Oregon Health & Science University, Portland, OR (US)

(72) Inventors: David Huang, Portland, OR (US); Yali Jia, Portland, OR (US); Jason Tokayer, Visalia, CA (US); Ou Tan, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 505 days.

(21) Appl. No.: 15/219,046

(22) Filed: Jul. 25, 2016

(65) Prior Publication Data

US 2016/0331229 A1   Nov. 17, 2016

Related U.S. Application Data

(63) Continuation of application No. 15/010,889, filed on Jan. 29, 2016, now abandoned, which is a (Continued)

(51) Int. Cl.
*A61B 3/10* (2006.01)
*A61B 3/12* (2006.01)
(Continued)

(52) U.S. Cl.
CPC .......... *A61B 3/1241* (2013.01); *A61B 3/0025* (2013.01); *A61B 3/102* (2013.01);
(Continued)

(58) Field of Classification Search
CPC ..... A61B 3/1241; A61B 3/0025; A61B 3/102; A61B 5/0066; A61B 5/7203; A61B 5/7207; A61B 5/7246
See application file for complete search history.

(56) References Cited

U.S. PATENT DOCUMENTS

| 6,685,646 B2 * | 2/2004 | Cespedes ................. A61B 8/06 600/454 |
| 2004/0225221 A1 | 11/2004 | Olsson |

(Continued)

FOREIGN PATENT DOCUMENTS

JP    2009-535164 A    10/2009

OTHER PUBLICATIONS

Jia, Yuli et al., "Split-Spectrum Amplitude-decorrelation Angiography with Optical Coherence Tomography," Optics Express, 2012, vol. 20, pp. 4710-4725.

(Continued)

*Primary Examiner* — Tse W Chen
*Assistant Examiner* — Milton Truong
(74) *Attorney, Agent, or Firm* — Schwabe, Williamson & Wyatt, P.C.

(57) ABSTRACT

Impaired intraocular blood flow within vascular beds in the human eye is associated with certain ocular diseases including, for example, glaucoma, diabetic retinopathy and age-related macular degeneration. A reliable method to quantify blood flow in the various intraocular vascular beds could provide insight into the vascular component of ocular disease pathophysiology. Using ultrahigh-speed optical coherence tomography (OCT), a new 3D angiography algorithm called split-spectrum amplitude-decorrelation angiography (SSADA) was developed for imaging microcirculation within different intraocular regions. A method to quantify SSADA results was developed and used to detect perfusion changes in early stage ocular disease. Associated embodiments relating to methods for quantitatively measuring blood flow at various intraocular vasculature sites, systems for practicing such methods, and use of such methods and systems for diagnosing certain ocular diseases are herein described.

24 Claims, 22 Drawing Sheets

Related U.S. Application Data continuation of application No. 14/023,190, filed on Sep. 10, 2013, now abandoned.

(60) Provisional application No. 61/699,257, filed on Sep. 10, 2012, provisional application No. 61/799,502, filed on Mar. 15, 2013.

(51) Int. Cl.

| | |
|---|---|
| A61B 5/026 | (2006.01) |
| A61B 5/0205 | (2006.01) |
| A61B 5/00 | (2006.01) |
| G06T 7/00 | (2017.01) |
| A61B 3/00 | (2006.01) |
| G01B 9/02 | (2006.01) |

(52) U.S. Cl.
CPC .......... *A61B 5/0066* (2013.01); *A61B 5/0205* (2013.01); *A61B 5/0261* (2013.01); *A61B 5/7207* (2013.01); *A61B 5/7246* (2013.01); *A61B 5/7278* (2013.01); *G01B 9/02004* (2013.01); *G01B 9/02044* (2013.01); *G01B 9/02091* (2013.01); *G06T 7/0016* (2013.01); *A61B 5/7203* (2013.01); *A61B 2576/02* (2013.01); *G06T 2207/10101* (2013.01); *G06T 2207/30041* (2013.01); *G06T 2207/30104* (2013.01)

(56) References Cited

U.S. PATENT DOCUMENTS

| | | | |
|---|---|---|---|
| 2007/0019208 A1 | 1/2007 | Toida et al. | |
| 2007/0291277 A1 | 12/2007 | Everett et al. | |
| 2008/0094613 A1 | 4/2008 | De Boer et al. | |
| 2008/0094637 A1* | 4/2008 | de Boer | A61B 5/0059 356/479 |
| 2009/0005691 A1* | 1/2009 | Huang | A61B 3/102 600/476 |
| 2009/0021724 A1 | 1/2009 | Mahadevan-Jansen et al. | |
| 2009/0149726 A1 | 6/2009 | Hyde et al. | |
| 2010/0103377 A1 | 4/2010 | Lesk | |
| 2010/0241001 A1* | 9/2010 | Palmeri | A61B 8/08 600/458 |
| 2011/0164218 A1* | 7/2011 | Ornberg | A61B 3/10 351/206 |
| 2011/0176716 A1* | 7/2011 | Kim | G06T 3/0075 382/131 |
| 2012/0004562 A1* | 1/2012 | Fingler | A61B 3/102 600/504 |
| 2012/0051664 A1 | 3/2012 | Gopalakrishnan et al. | |
| 2012/0307014 A1* | 12/2012 | Wang | A61B 3/102 348/46 |

OTHER PUBLICATIONS

Zhi, Zhongwei et al., "Volumetric and Quantitative Imaging of Retinal Blood Flow in Rats with Optical Microangiography," Biomedical Optics Express, vol. 1, No. 3, Feb. 15, 2011, p. 579.

Jia, Yali et al., "Quantitative OCT Angiography of Optic Nerve Head Blood Flow," Biomedical Optics Express, vol. 3, No. 12, Nov. 7, 2012, p. 3127.

Zhi, Zhongwei et al., "Impact of Intraocular Pressure on Changes of Blood Flow in the Retina, Choroid, and Optic Nerve Head in Rats Investigated by Optical Microangiography," Biomedical Optics Express, vol. 3, No. 9, Aug. 24, 2012, p. 2220.

Baumann, Bernhard et al., "Total Retinal Blood Flow Measurement with Ultrahigh Speed Swept Source/Fourier Domain OCT," Biomedical Optics Express, vol. 2, No. 6, May 13, 2011, p. 1539.

* cited by examiner

FIG. 1

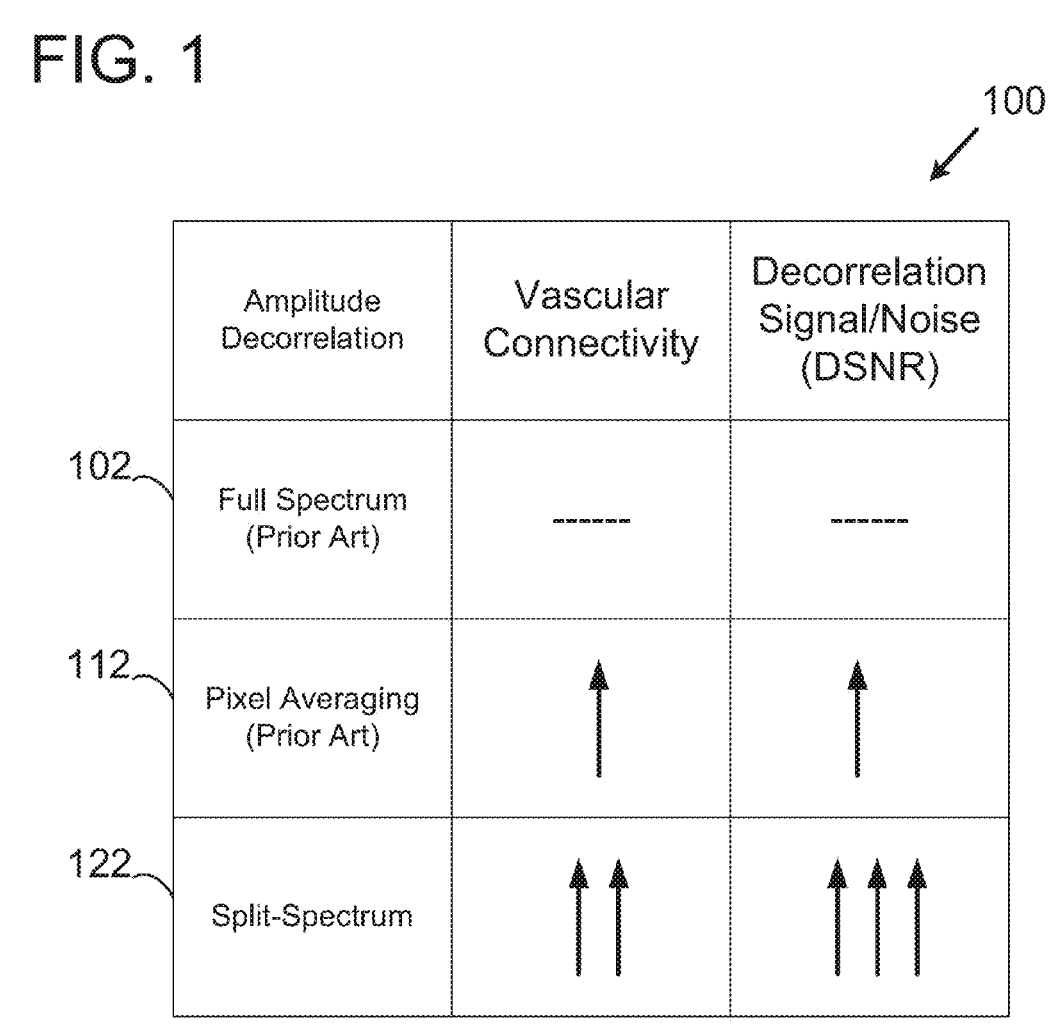

| Amplitude Decorrelation | Vascular Connectivity | Decorrelation Signal/Noise (DSNR) |
|---|---|---|
| Full Spectrum (Prior Art) | ------ | ------ |
| Pixel Averaging (Prior Art) | ↑ | ↑ |
| Split-Spectrum | ↑↑ | ↑↑↑ |

Figures 17 A-D

QUANTIFICATION OF LOCAL CIRCULATION WITH OCT ANGIOGRAPHY

CROSS-REFERENCE TO RELATED APPLICATIONS

The present application is a continuation of U.S. patent application Ser. No. 15/010,889 filed on Jan. 29, 2016, which is a continuation of U.S. patent application Ser. No. 14/023,190 filed on Sep. 10, 2013, which claims benefit to U.S. Provisional Patent Application No. 61/699,257 filed Sep. 10, 2012, entitled "QUANTIFICATION OF LOCAL CIRCULATION WITH OCT ANGIOGRAPHY", and to U.S. Provisional Patent Application No. 61/799,502 filed Mar. 15, 2013, entitled "IN VIVO QUANTITATIVE OPTICAL FLOW IMAGING". Priority to these applications is expressly claimed, and the disclosures of these applications are herein incorporated by reference in their entirety.

ACKNOWLEDGMENT OF GOVERNMENT SUPPORT

This invention was made with government support under grant numbers R01-EY013516 awarded by the National Institutes of Health. The government has certain rights in the technology.

TECHNICAL FIELD

This disclosure relates generally to the field of biomedical imaging, and more specifically to methods, apparatuses, and systems associated with optical coherence tomography and angiography.

BACKGROUND

Diabetic retinopathy, age-related macular degeneration and glaucoma are the typical ocular diseases in which vascular disorders and impaired circulation have been observed. For example, an increasing body of evidence suggests that dysfunction of ocular microcirculation in the optic nerve influences the progression of glaucoma. Quantification of ocular circulation is therefore important for the diagnosis of ophthalmic diseases.

Currently, a number of methods have been used for measuring ocular perfusion. Fluorescein angiography (FA) provides useful qualitative information in health and disease; however, it only shows the superficial retinal vessels and does not assess deep perfusion, such as the microcirculation in optic nerve head (ONH), choroidal blood flow. Additionally, injection of dye can cause nausea and anaphylaxis, making it unsuitable as a tool for routine glaucoma assessment. Both laser Doppler flowmetry [e.g. Heidelberg Retinal Flowmeter (HRF)], which samples capillary flow over a small retinal area, and laser speckle flowgraphy, which provides a spot sample of blood velocity, can show differences between diseases and normal groups. However the measurements provided by these methods are too variable for diagnostic application due to dependence on the signal strength and the location of the small sampled area. Magnetic resonance imaging (MRI) has been proposed to quantitatively image ONH perfusion; however, the major limiting factor with this method is the small size of the ONH and limited resolution to detect focal or mild circulatory insufficiency.

Optical coherence tomography (OCT) is an imaging technique that has been widely used for diagnosis and management of ocular diseases. As a coherence detection technique, OCT can detect the Doppler frequency shift of the backscattered light that provides information on blood flow. Doppler OCT has been used for measuring total human retinal blood flow (TRBF) in patients with glaucoma, optic neuropathy, and diabetic retinopathy. With this method, global blood flow from central retinal vessels can be quantified, but local microcirculation cannot be resolved because the velocity range is too low for accurate Doppler measurement. To measure local microcirculation, we recently developed the split-spectrum amplitude-decorrelation angiography (SSADA) algorithm that provides high quality three-dimensional (3D) angiography using ultrahigh speed OCT. Because SSADA is based on the variation of reflectance in resolution cells of isotropic dimensions, it is equally sensitive to transverse and axial movements. Thus it may be able to provide more impartial estimates of local microvascular perfusion that are independent of beam incidence angle. In contrast, both Doppler and phase-variance OCT angiography are more sensitive to axial flow than to transverse flow. Therefore SSADA may be a good basis for quantitative angiography of the microcirculation within different vascular beds.

In vivo three-dimensional mapping of biologic tissue and vasculature is difficult due to the highly-scattering and absorptive nature of biologic tissue. Some current methods have slow scanning speeds making in vivo three-dimensional imaging difficult. Some other techniques having faster scanning speeds are still lacking due to their inability to scan deeply into biologic tissue without producing overlapped images, requiring the use of invasive procedures to scan the tissue of interest. Many techniques aimed at deeper imaging generally cannot provide deep imaging of tissue having moving material (e.g., blood flow). Therefore, methods to effectively image structure and/or tissue movement, such as blood flow, are of substantial clinical importance.

Optical coherence tomography (OCT) is an imaging modality for high-resolution, depth-resolved cross-sectional, and 3-dimensional (3D) imaging of biological tissue. Among its many applications, ocular imaging in particular has found widespread clinical use. In the last decade, due to the development of light source and detection techniques, Fourier-domain OCT, including spectral (spectrometer-based) OCT and swept-source OCT, have demonstrated superior performance in terms of sensitivity and imaging speed over those of time-domain OCT systems. The high-speed of Fourier-domain OCT has made it easier to image not only structure, but also blood flow. This functional extension was first demonstrated by Doppler OCT which images blood flow by evaluating phase differences between adjacent A-line scans. Although Doppler OCT is able to image and measure blood flow in larger blood vessels, it has difficulty distinguishing the slow flow in small blood vessels from biological motion in extravascular tissue. In the imaging of retinal blood vessels, Doppler OCT faces the additional constraint that most vessels are nearly perpendicular to the OCT beam, and therefore the detectability of the Doppler shift signal depends critically on the beam incident angle. Thus, other techniques that do not depend on beam incidence angle are particularly attractive for retinal and choroidal angiography.

Several OCT-based techniques have been successfully developed to image microvascular networks in human eyes in vivo. One example is optical microangiography (OMAG), which can resolve the fine vasculature in both retinal and choroid layers. OMAG works by using a modified Hilbert transform to separate the scattering signals from static and moving scatters. By applying the OMAG algorithm along the slow scanning axis, high sensitivity imaging of capillary flow can be achieved. However, the high-sensitivity of OMAG requires precise removal of bulk-motion by resolving the Doppler phase shift. Thus, it is susceptible to artifacts from system or biological phase instability. Other related methods such as phase variance and Doppler variance have been developed to detect small phase variations from microvascular flow. These methods do not require non-perpendicular beam incidence and can detect both transverse and axial flow. They have also been successful in visualizing retinal and choroidal microvascular networks. However, these phase-based methods also require very precise removal of background Doppler phase shifts due to the axial movement of bulk tissue. Artifacts can also be introduced by phase noise in the OCT system and transverse tissue motion, and these also need to be removed.

To date, most of the aforementioned approaches have been based on spectral OCT, which provides high phase stability to evaluate phase shifts or differentiates the phase contrast resulting from blood flow. Compared with spectral OCT, swept-source OCT introduces another source of phase variation from the cycle-to-cycle tuning and timing variabilities. This makes phase-based angiography noisier. To use phase-based angiography methods on swept-source OCT, more complex approaches to reduce system phase noise are required. On the other hand, swept-source OCT offers several advantages over spectral OCT, such as longer imaging range, less depth-dependent signal roll-off, and less motion-induced signal loss due to fringe washout. Thus an angiography method that does not depend on phase stability may be the best choice to fully exploit the advantages of swept-source OCT. In this context, amplitude-based OCT signal analysis may be advantageous for ophthalmic microvascular imaging.

One difficulty associated with OCT's application in microvascular imaging comes from the prevalent existence of speckle in OCT images obtained from in vivo or in situ biological samples. Speckle is the result of the coherent summation of light waves with random path lengths and it is often considered as a noise source which degrades the quality of OCT images. Various methods have been developed to reduce speckle in spatial domain, such as angle compounding, spectral compounding, and strain compounding. Speckle adds to "salt-and-pepper-like" noise to OCT images and induces random modulation to interferometric spectra which can significantly reduce contrast.

In spite of being a noise source, speckle also carries information. Speckle patterns form due to the coherent superposition of random phasors. As a result of speckle, the OCT signal becomes random in an area that is macroscopically uniform. If a sample under imaging is static, the speckle pattern is temporally stationary. However, when photons are backscattered by moving particles, such as red blood cells in flowing blood, the formed speckle pattern will change rapidly over time. Speckle decorrelation has long been used in ultrasound imaging and in laser speckle technique to detect optical scattering from moving particles such as red blood cells. This phenomenon is also clearly exhibited by real-time OCT reflectance images. The scattering pattern of blood flow varies rapidly over time. This is caused by the fact that the flow stream drives randomly distributed blood cells through the imaging volume (voxel), resulting in decorrelation of the received backscattered signals that are a function of scatterer displacement over time. The contrast between the decorrelation of blood flow and static tissue may be used to extract flow signals for angiography.

The speckle phenomenon has been used in speckle variance OCT for the visualization of microvasculature. Speckle patterns at areas with flowing blood have a large temporal variation, which can be quantified by inter-frame speckle variance. This technique termed "speckle variance" has been used with swept-source OCT demonstrating a significant improvement in capillary detection in tumors by calculation of the variance of the OCT signal intensity. A key advantage of the speckle variance method is that it does not suffer from phase noise artifacts and does not require complex phase correction methods. Correlation mapping is another amplitude-based method that has also recently demonstrated swept-source OCT mapping of animal cerebral and human cutaneous microcirculation in vivo. These amplitude-based angiography methods are well suited to swept-source OCT and offer valuable alternatives to the phase-based methods. However, such methods still suffer from bulk-motion noise in the axial dimension where OCT resolution is very high. Therefore, an amplitude-based swept-source angiography method that is able to reduce bulk-motion noise without significant sacrifice in the flow signal would be optimal. For example, imaging of retinal and choroidal flow could be particularly improved with such noise reduction, as in the ocular fundus the flow signal is predominantly in the transverse rather than axial dimension.

While improving qualitative blood flow measurement through noise reduction methods has immense value, determining quantitative blood flow measurement in regions of interest is highly desirable clinically. To date, while several methods exist to measure global retinal blood flow, they have significant limitations and are not used clinically. For example, ultrasound color Doppler imaging does not have sufficient spatial resolution to measure retinal vessels. It measures velocity and resistive indices in large retrobulbar vessels. Although studies have shown differences between normal and glaucoma groups using ultrasound color Doppler imaging, variability in measurements has limited its potential for clinical diagnosis. Bidirectional laser Doppler velocimetry can measure velocity and flow in individual retinal vessels, but measurement of total retinal blood flow is too time consuming to be practical. Dicon's pulsatile ocular blood flow analyzer can analyze intraocular pressure, but has been shown to be a poor correlate of ocular circulation. Finally, dual-angle Doppler OCT has the limitation of requiring special hardware that is not compatible with existing commercial OCT designs.

As noted above, Doppler OCT, on its own, has difficulty distinguishing the slow flow in small blood vessels from biological motion in extravascular tissue, as well as has difficulty detecting and defining vessel anatomy due to most vessels being nearly perpendicular to the OCT beam. However, Doppler shift can provide valuable quantitative velocity information. Thus, an optimal bulk-noise reduction amplitude-based swept-source angiography method used in combination with Doppler OCT (e.g., via dual scanning, done simultaneously or near simultaneously) could allow for measurement of total retinal blood flow (TRBF), including both vein and artery measurement around the optic disc.

SUMMARY

As described below, a new quantitative system has been established for making quantitative ocular blood flow measurements. Specifically, the methods described herein are able to measure circulation in ONH (e.g. whole disc/temporal ellipse, peripapillary retina, peripapillary choroid) and macula (e.g. macular retina, macular choroid, fovea avascular zone and the area of non-perfusion). Quantification of different circulation obtained from patients having an ocular disease compared with the result from normal subjects are herein described.

One embodiment is directed to methods for quantitatively measuring blood flow in an ocular vascular bed. In certain embodiments, the method for quantitatively measuring blood flow in an ocular vascular bed may comprise the steps of selecting an ocular vascular bed from which to quantitatively measure blood flow, scanning the ocular vascular bed to obtain M-B scans of OCT spectrum therefrom, splitting the M-B scans of OCT spectrum into M spectral bands and determining a quantitative measurement of blood flow from the M spectral bands. In additional embodiments, the step of splitting the M-B scans of the OCT spectrum into M spectral bands may comprise creating overlapping filters covering the OCT spectrum, and filtering the OCT spectrum with the overlapping filters. In yet further embodiments, the step of determining a quantitative measurement of blood flow from the M spectral bands may comprise creating decorrelation images for the M spectral bands and combining the decorrelation images for the M spectral bands to create a flow image and/or the step of creating decorrelation images for the M spectral bands may comprise determining amplitude information for each spectral band and calculating decorrelation between adjacent amplitude frames for each spectral band.

Yet other embodiments are directed to methods for quantitatively measuring blood flow in an ocular vascular bed as described above that further comprise the step of removing background noise. The methods described herein may optionally also comprise combining the decorrelation images for the M spectral bands to create a flow image that comprises averaging the decorrelation images for each spectral band to create an average decorrelation image for each spectral band and averaging the averaged decorrelation images from the M spectral bands. The ocular vascular bed from which quantitative blood flow measurements are obtained may include the ocular nerve head, the macula, the ocular disc, the temporal ellipse, the peripapillary retina, the peripapillary choroid, the macular retina, the macular choroid, the fovea avascular zone, or the area of non-perfusion.

Other embodiments are directed to use of the herein described methods for quantitatively measuring blood flow in an ocular vascular bed for the purpose of diagnosing an ocular disease. In this regard, it is noted that ocular diseases such as glaucoma, diabetic retinopathy and age-related macular degeneration are associated with impaired intraocular blood flow and circulation.

Yet further embodiments are directed to specific systems useful for quantitatively measuring blood flow in an intraocular vascular bed. In certain embodiments, such systems may comprise an optical coherence tomography apparatus and one or more processors coupled to the OCT apparatus and adapted to cause that apparatus to obtain M-B scans of OCT spectrum from the ocular vascular bed, split the M-B scans of OCT spectrum into M spectral bands, and determine a quantitative measurement of blood flow from the M spectral bands.

Additional embodiments will be readily apparent to one skilled in the art upon reading the present specification.

BRIEF DESCRIPTION OF THE DRAWINGS

Embodiments described herein will be readily understood by the following detailed description in conjunction with the accompanying drawings. Embodiments are illustrated by way of example and not by way of limitation in the figures of the accompanying drawings.

FIG. 1 is a chart comparing prior art techniques with those described herein with regard to vascular connectivity and decorrelation signal/noise (DSNR).

DETAILED DESCRIPTION

Figure 2:
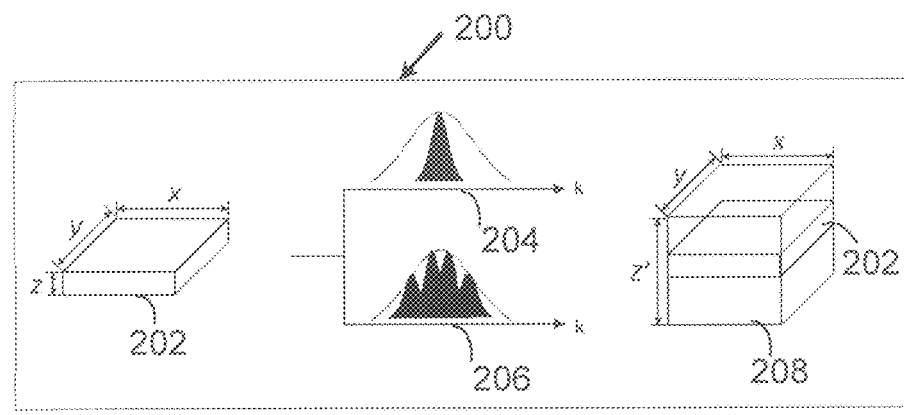
FIG. 2 schematically illustrates modification of an OCT imaging resolution cell to create an isotropic resolution cell utilizing a band-pass filter.

In the following detailed description, reference is made to the accompanying drawings which form a part hereof. It is to be understood that other embodiments may be utilized and structural or logical changes may be made.

Various operations may be described as multiple discrete operations in turn, in a manner that may be helpful in understanding embodiments described herein; however, the order of description should not be construed to imply that these operations are order dependent.

The description may use perspective-based descriptions such as up/down, back/front, and top/bottom. Such descriptions are merely used to facilitate the discussion and are not intended to restrict the application of embodiments described herein.

The description may use the phrases "in an embodiment," or "in embodiments," which may each refer to one or more of the same or different embodiments. Furthermore, the terms "comprising," "including," "having," and the like, as used with respect to embodiments described herein, are synonymous.

A phrase in the form of "A/B" means "A or B." A phrase in the form "A and/or B" means "(A), (B), or (A and B)." A phrase in the form "at least one of A, B and C" means "(A), (B), (C), (A and B), (A and C), (B and C) or (A, B and C)." A phrase in the form "(A) B" means "(B) or (A B)," that is, A is optional.

In various embodiments described herein, methods, apparatuses, and systems for biomedical imaging are provided. In exemplary embodiments described herein, a computing system may be endowed with one or more components of the disclosed articles of manufacture and/or systems and may be employed to perform one or more methods as disclosed herein.

In various embodiments, structure and/or flow information of a sample may be obtained using optical coherence tomography (OCT) (structure) and OCT angiography (structure and flow) imaging based on the detection of spectral interference. Such imaging may be two-dimensional (2-D) or three-dimensional (3-D), depending on the application. Structural imaging may be of an extended depth range relative to prior art methods, and flow imaging may be performed in real time. One or both of structural imaging and flow imaging as disclosed herein may be enlisted for producing 2-D or 3-D images.

Unless otherwise noted or explained, all technical and scientific terms used herein are used according to conventional usage and have the same meaning as commonly understood by one of ordinary skill in the art which the disclosure belongs. Although methods, systems, and apparatuses/materials similar or equivalent to those described herein can be used in the practice or testing of the present disclosure, suitable methods, systems, and apparatuses/materials are described below.

All publications, patent applications, patents, and other references mentioned herein are incorporated by reference in their entirety. In case of conflict, the present specification, including explanation of terms, will control. In addition, the methods, systems, apparatuses, materials, and examples are illustrative only and not intended to be limiting.

In order to facilitate review of the various embodiments of the disclosure, the following explanation of specific terms is provided:

A-scan: A reflectivity profile that contains information about spatial dimensions and location of structures with an item of interest (e.g., an axial depth scan).

Autocorrelation: A cross-correlation of a signal with itself; the similarity between observations as a function of the time separation between them. For example, autocorrelation can be used to find repeating patterns, such as the presence of a periodic signal which has been buried under noise, or used to identify the missing fundamental frequency in a signal implied by its harmonic frequencies.

B-scan: A cross-sectional tomograph that may be achieved by laterally combining a series of axial depth scans (e.g., A-scans).

Cross-correlation: A measure of similarity of two waveforms as a function of a time-lag applied to one of the waveforms.

Decorrelation: A process that is used to reduce autocorrelation within a signal, or cross-correlation within a set of signals, while preserving other aspects of the signal. For example, decorrelation can be used to enhance differences found in each pixel of an image. A measure of a lack of correlation or similarity between corresponding pixels in two images can also describe decorrelation. The end result of a decorrelation process is that faint information within a signal may be enhanced to bring out (e.g., present) subtle differences that may be meaningful. For example, one can calculate decorrelation to find a difference between images.

Illustrated in FIG. 1 is a comparison chart 100 of prior art amplitude-based OCT signal analysis methods and the embodiments described herein based on vascular connectivity and decorrelation signal/noise (DSNR). Full-spectrum decorrelation method 100, for example, can be utilized as the baseline value for comparison purposes, however, as described previously, it is sensitive to axial bulk motion causing significant noise in the resulting images produced. In pixel averaging method 112 the signal in several adjacent pixels is combined resulting in an improvement of decorrelation signal-to-noise ratio (DSNR). The improved DSNR of pixel averaging method 112 in turn leads to higher quality images of microcirculation (compared to full-spectrum decorrelation method 100), which can be assessed by measuring the vasculature of the microvascular network revealed in the OCT angiograms. As described herein, split-spectrum decorrelation 122 further improves DSNR (compared to the improvement offered by pixel averaging method 112) by reducing the noise due to axial bulk motion. This can be accomplished by the methods described herein below (e.g., reducing the axial dimension of the effective resolution cell).

The improved DSNR of split-spectrum decorrelation method 122 in turn leads to even higher quality images of microcirculation (compared to full-spectrum decorrelation method 100 and pixel averaging method 112), which can be assessed by measuring the vasculature of the microvascular network revealed in the OCT angiograms. Such an improvement, can allow for images and information useful in for diagnostic and management of diseases in the eye, as well as investigations and analysis of circulation, angiogenesis and the other blood flow imaging analysis. Additionally, the split-spectrum decorrelation 122 could be used to obtain angiography images that could be used to replace fluorescein and indocyanine green angiographies, with the additional advantage of being intrinsically 3-dimensional rather than 2-dimensional. Additional uses can include, but not be limited to, imaging of blood flow in other biological tissue and the imaging of flow in any system, living or nonliving.

In more detail, prior art full-spectrum decorrelation 102 achieves decorrelation purely through process the amplitude signal and does not require phase information. To evaluate the flow signals coming from the scattering tissue, an average decorrelation image $\overline{D}(x,z)$ at each position is obtained by averaging N−1 decorrelation image frames computed from N reflectance amplitude images frames from M-B mode scanning. Each decorrelation frame is computed from 2 adjacent amplitude frames: $A_n(x,z)$ and $A_{n+1}(x,z)$. Using the full spectrum decorrelation method 102, the decorrelation image it is given by the following equation:

$$\overline{D}(x, z) = 1 - \frac{1}{N-1} \sum_{n=1}^{N-1} \frac{A_n(x, z)A_{n+1}(x, z)}{\left[\frac{1}{2}A_n(x, z)^2 + \frac{1}{2}A_{n+1}(x, z)^2\right]} \quad (1)$$

$(N = 8)$ where x and z are lateral and depth indices of the B-scan images and n denotes the B-scan slice index. In this full spectrum equation, the decorrelation signal-to-noise ratio acquired from full spectrum can only be increased by increasing the number N of B-scans taken at the same position. However, more scans require more imaging time which may not be practical.

In more detail, prior art pixel averaging method 112 can produce decorrelation images given by the following equation:

$$\overline{D}(x, z) = 1 - \frac{1}{N-1} \frac{1}{PQ} \quad (2)$$

$$\sum_{n=1}^{N-1} \sum_{p=1}^{P} \sum_{q=1}^{Q} \frac{A_n(x+p, z+q)A_{n+1}(x+p, z+q)}{\left[\frac{1}{2}A_n(x+p, z+q)^2 + \frac{1}{2}A_{n+1}(x+p, z+q)^2\right]}$$

$(P = 1, Q = 4, N = 8)$ where P and Q are the averaging window widths in the X and Z directions, as described in J. Enfield, E. Jonathan, and M. Leahy, "In vivo imaging of the microcirculation of the volar forearm using correlation mapping optical coherence tomography (cmoct)," Biomed. Opt. Express 2(5), 1184-1193 (2011). To suppress the spurious noise and discontinuities in the vasculature, P by Q window moving average can be implemented over the X-Z 2D map. To fairly compare the prior art pixel averaging method 112 with the split-spectrum decorrelation 122 described herein, a 1 by 4 window can be created, which means pixel-averaging is only applied along the Z direction, the same direction used for splitting the spectrum in split-spectrum decorrelation 122

In more detail, split-spectrum decorrelation 122 can produce decorrelation images given by the following equation:

$$\overline{D}(x, z) = \quad (3)$$

$$1 - \frac{1}{N-1} \frac{1}{M} \sum_{n=1}^{N-1} \sum_{m=1}^{M} \frac{A_n(x, z)A_{n+1}(x, z)}{\left[\frac{1}{2}A_n(x, z)^2 + \frac{1}{2}A_{n+1}(x, z)^2\right]}$$

$(M = 4, N = 8)$

After splitting the spectrum by applying M (for example, M can =4 as described in an exemplary example below) equally spaced bandpass filters, M individual decorrelation images can be obtained between each pair of B-scans, which can then be averaged along both the lateral (X) and axial (Z) directions to increase DSNR. In split-spectrum decorrelation 122, the average decorrelation image $\overline{D}(x,z)$ can be described as the average of decorrelation images from M spectral bands. By increasing the number M (up to a point), the decorrelation signal-to-noise ratio can be improved without increasing the scan acquisition time.

Whichever decorrelation method is used (full-spectrum 102, pixel-averaging 112, and split-spectrum 122) the resulting average decorrelation image frame $\overline{D}(x,z)$ should be a value between zero and one, indicating weak and strong decorrelation, respectively. By describing the decorrelation methods in such detail above, it is possible to compare the methods to one another based on the resulting decorrelation images obtained as illustrated in chart 100 of FIG. 1. The split-spectrum method 122 suppresses noise from axial bulk motion and, in addition, makes use of information in the full k spectrum resulting in superior decorrelation signal-to-noise ratio for flow detection. Utilizing the split-spectrum method 122, axial bulk motion can be suppressed by the use of spectral (k) bandpass filters that increase the axial dimension of the resolution cell so that it can be equal (or substantially equal) to the transverse dimension of the resolution cell.

Illustrated in FIG. 2 is diagram 200 visually depicting modification of an OCT imaging resolution cell 202 via two distinct and separate techniques (band-pass filtering 204 and split-spectrum 206) to create an isotropic resolution cell 208. Each pixel in a B-scan OCT image is formed from backscattered signals of a 3D volume in space, referred to as a resolution cell (e.g., imaging resolution cell 202 in FIG. 2). The statistical changes in the envelope intensity are related to the motion of scatterers through the OCT resolution cell. For a typical swept-source OCT setup, the axial (Z direction) resolution, determined by the source central wavelength and its spectral bandwidth, is much higher than the lateral resolution determined by the laser beam profile in both X and Y directions. For example, in common swept source OCT systems, using the full-width-half-maximum (FWHM) amplitude profile definition, the axial resolution (~5 μm) is four times higher than the lateral resolution (~18 μm) if both are defined as full-width-half-maximum amplitude profiles (e.g., imaging resolution cell 202 depicts x=y=4z). This anisotropic resolution cell, with higher axial than transverse resolution, will result in higher decorrelation sensitivity for axial motion. In the fundus, ocular pulsation related to heart beat, driven by the retrobulbar orbital tissue, mainly occurs along the axial direction. The anisotropic resolution cell of retinal OCT imaging is very sensitive to this axial motion noise. On the other hand, retinal and choroidal blood flow vectors are primarily transverse to the OCT beam, along the wider (less sensitive) dimensions of the OCT resolution cell. Therefore, to improve the signal-to-noise ratio (SNR) of flow detection, it is desirable to lower the axial resolution and dampen the axial decorrelation sensitivity. This reduces the axial motion noise without sacrificing the transverse flow signal.

One straightforward way to achieve this resolution modification is band-pass filtering of the spectral interferogram (e.g., band-pass filtering 204). Unfortunately, this also sacrifices most of the speckle information in the spectral interferogram and decreases the flow signal. Thus, this is not an effective way to increase the SNR of flow (decorrelation) detection. A better way to decrease axial resolution without losing any speckle information is to split the spectrum into different frequency bands (e.g., split-spectrum 206) and calculate decorrelation in each band separately. The decorrelation (flow) images from the multiple spectral bands can then be averaged together to make full use of the speckle information in the entire OCT spectrum. The details of the split-spectrum procedure are explained herein and below (e.g., split-spectrum decorrelation 122 of FIG. 1 can be utilized).

Figure 3:
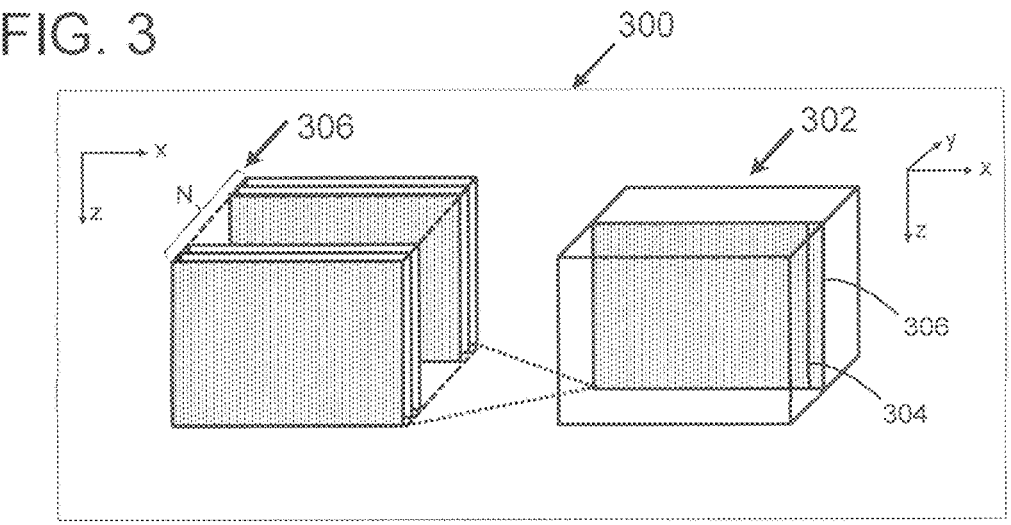
FIG. 3 schematically illustrates M-B-scan mode for acquiring OCT spectrum.

Illustrated in FIG. 3 is a visual 300 of one 3D volumetric data 302 comprising data obtained via an exemplary embodiment M-B-scan mode from an OCT system. N consecutive B-scans at a single Y position comprise M-B-scan 306 (e.g., in some exemplary embodiments described herein, N=eight (8), but is not limited to any specific N). Therefore, for each 3D volumetric data 302, in the fast scan (x) axis, a single B-scan comprises a plurality of A-scans 304, and in the slow scan (y) axis, there are a number of M-B-scans 306 comprising N consecutive B-scans.

Figure 4:
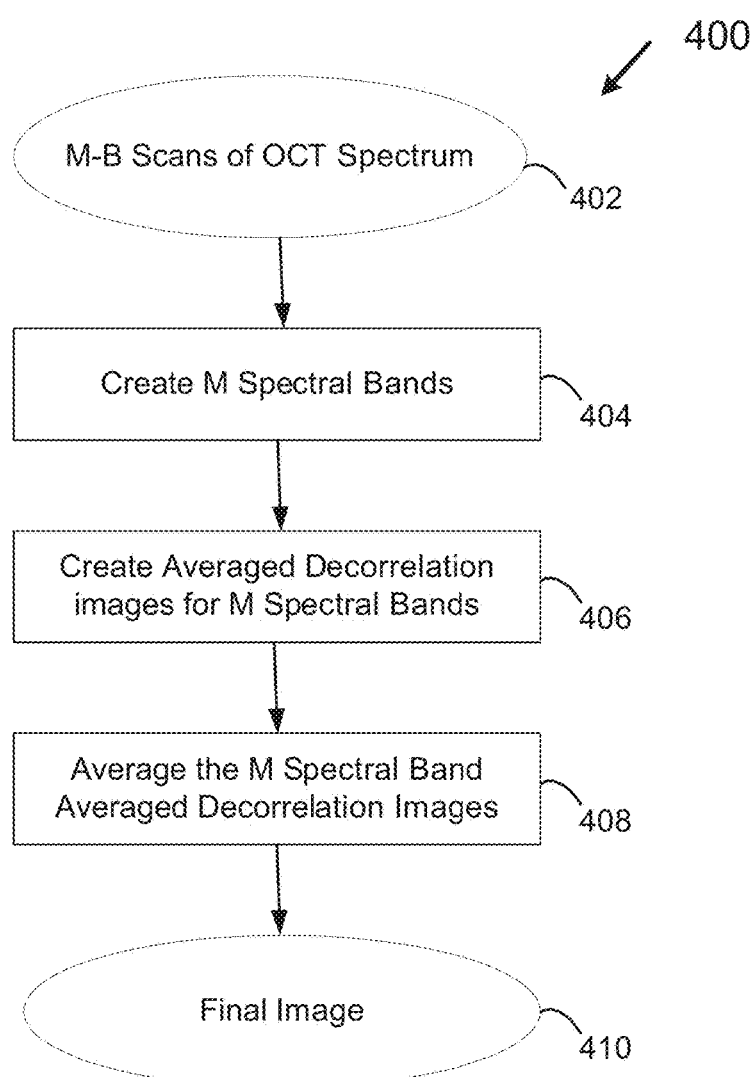
FIG. 4 is a flowchart showing an exemplary method for creating a decorrelation (flow) image that uses split-spectrum techniques and the full information in the entire OCT spectral range.

FIG. 4 shows an exemplary method 400 for creating a decorrelation (flow) image that uses split-spectrum techniques and the full information in the entire OCT spectral range. The method 400 can be performed, for example, by in vivo imaging systems described herein below. Portions of method 400 and any of the other methods (or portion of methods) described herein can be performed by computer-executable instructions stored on computer-readable media and articles of manufacture for in vivo imaging.

At 402, M-B scans of OCT spectrum are received. For example, M-B scans as depicted in visual 300 of FIG. 3 can be received from an OCT in vivo imaging system.

At 404, M spectral bands can be created from the M-B scans of OCT spectrum 402. For example, split spectrum 206 of FIG. 2 can be utilized to create the M spectral bands.

At 406, averaged decorrelation images for each spectral band of the M spectral bands can be created. For example, split spectrum decorrelation 122 described in FIG. 1 can be utilized to create decorrelation images for the M spectral bands and then for each spectral band those decorrelation images can be averaged.

At 408, the averaged decorrelation images for each spectral band created at 406 can be averaged to create a single final image (e.g., final decorrelation image) 410.

Figure 5:
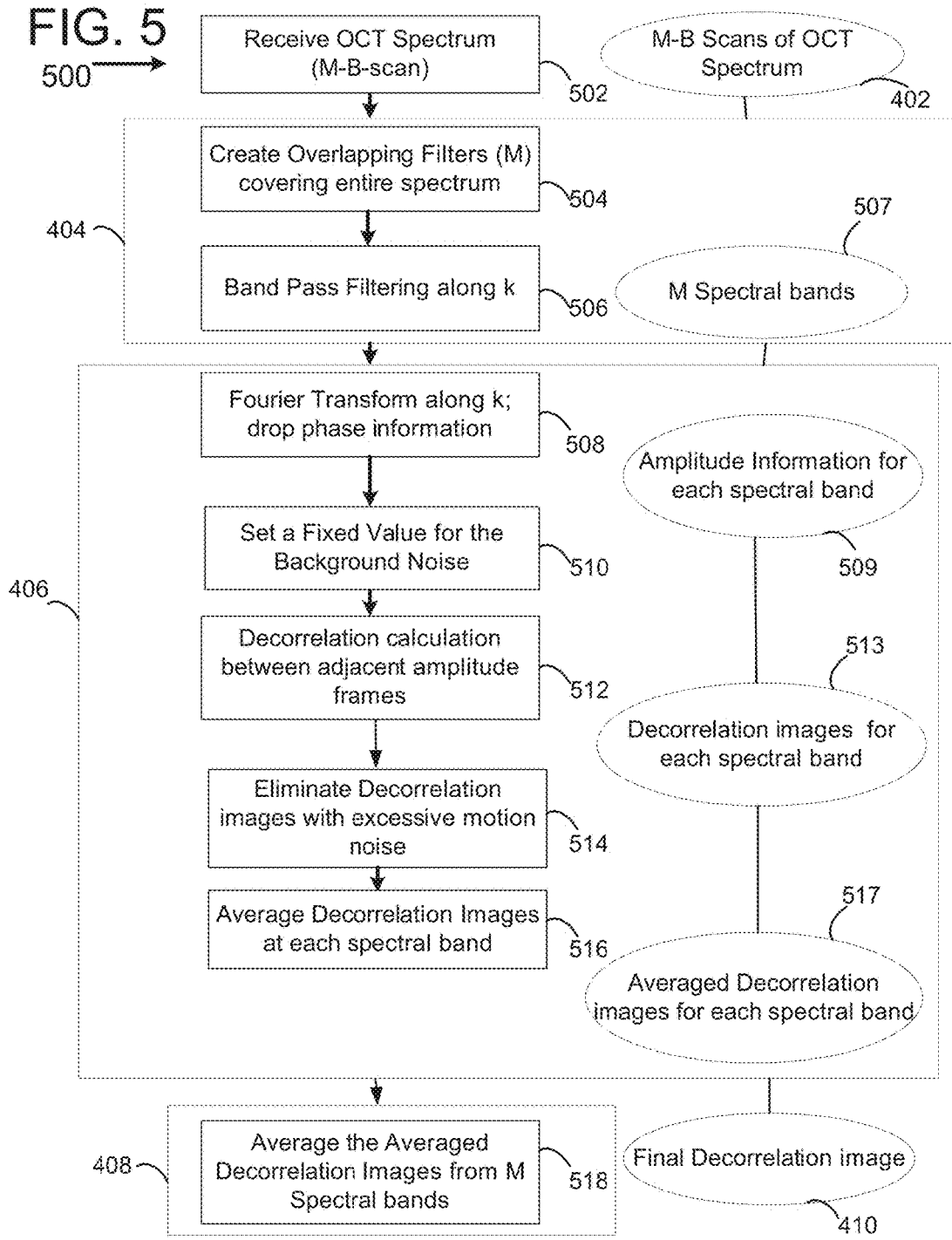
FIG. 5 is a flowchart showing additional exemplary methods of the exemplary method of FIG. 4.

FIG. 5 shows additional exemplary methods 500, including reference to similar methods within method 400 of FIG. 4, for creating a decorrelation (flow) image that uses split-spectrum techniques and the full information in the entire OCT spectral range. The method 500 can be performed, for example, by in vivo imaging systems described herein below. Portions of method 500 and any of the other methods (or portion of methods) described herein can be performed by computer-executable instructions stored on computer-readable media and articles of manufacture for in vivo imaging.

Figure 6:
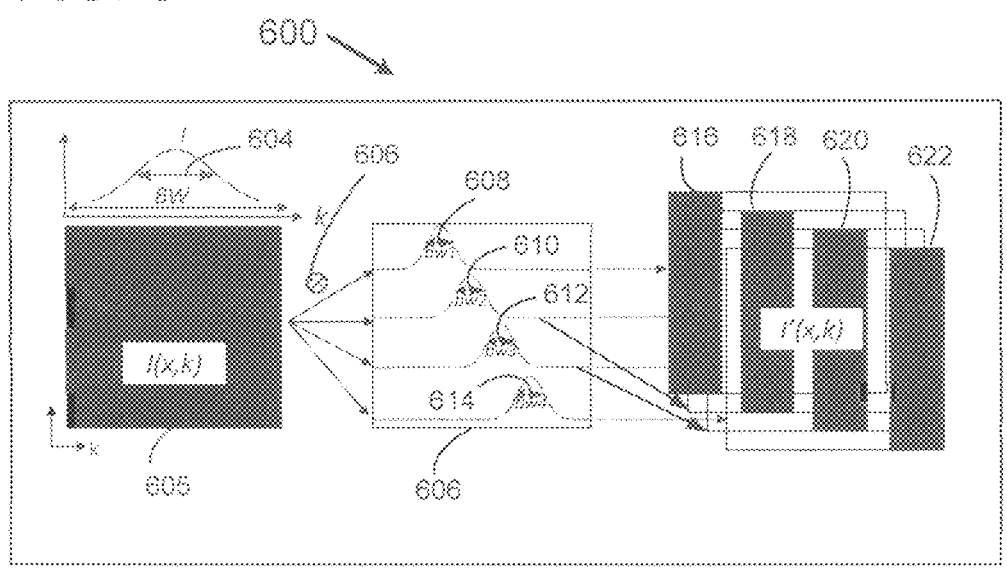
FIG. 6 schematically illustrates a 2D spectral interferogram split into different frequency bands.

FIG. 6 schematically illustrates via visual 600 a 2D spectral interferogram split into different frequency bands as described in methods 400 of FIG. 4 and 500 of FIG. 5.

Figure 7:
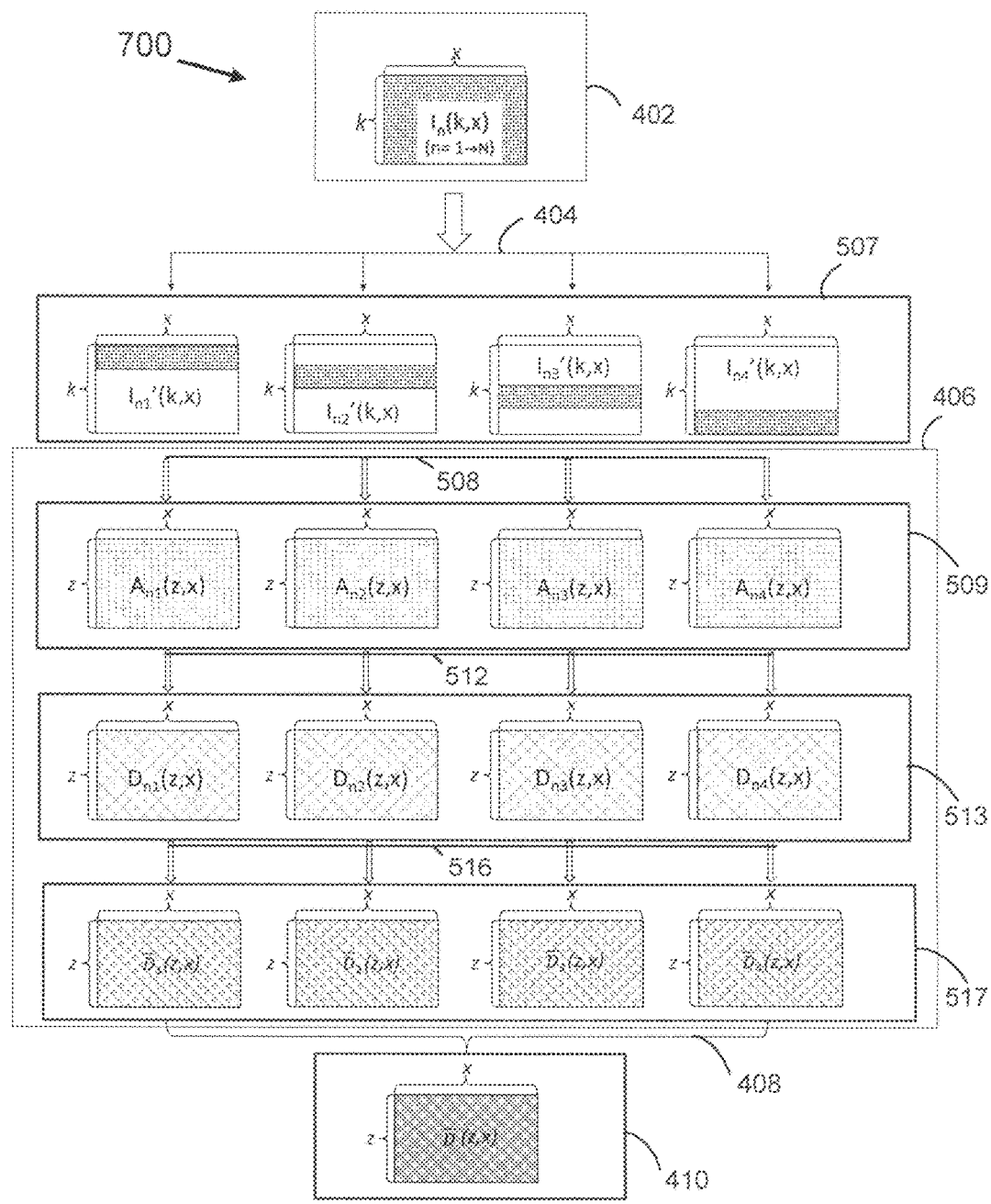
FIG. 7 schematically illustrates the methods of FIG. 4 and FIG. 5 for creating a decorrelation (flow) image that uses split-spectrum techniques and the full information in the entire OCT spectral range.

FIG. 7 schematically illustrates via visual 700 the methods 400 of FIG. 4 and 500 of FIG. 5 for creating a decorrelation (flow) image that uses split-spectrum techniques and the full information in the entire OCT spectral range.

Figure 8:
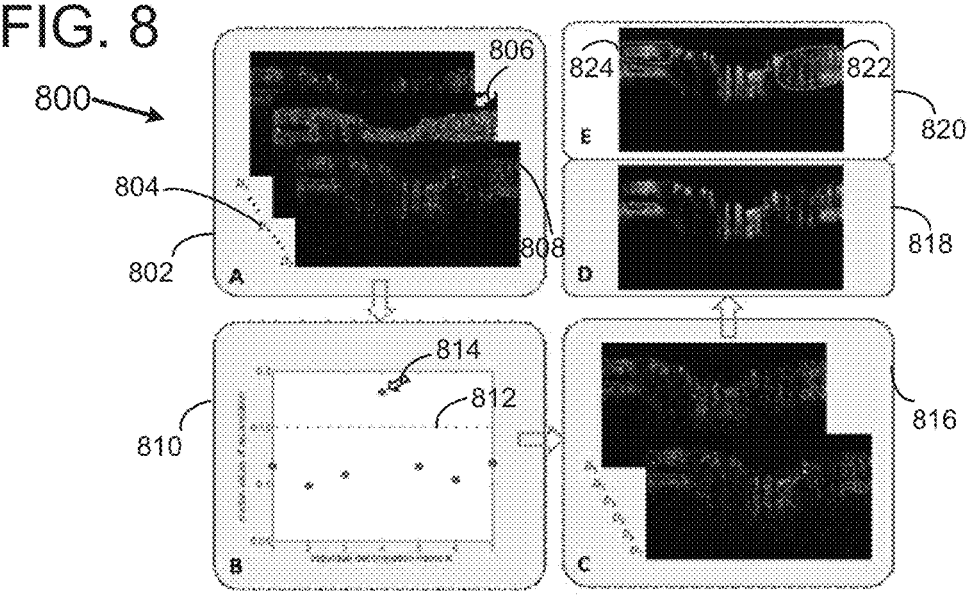
FIG. 8 is a flowchart showing an exemplary method for eliminating decorrelation images with excessive motion noise.

FIG. 8 is a flowchart 800 showing an exemplary method for eliminating decorrelation images with excessive motion noise (e.g., as described in method 500 of FIG. 5).

Continuing with the method 500 of FIG. 5, at 502, M-B scans of OCT spectrum are received. For example, M-B scans of OCT spectrum 402 can be received from an OCT in vivo imaging system, as depicted in FIG. 7. In more detail, for example, spectral interference signal recorded by a high speed digitizer in swept-source OCT, after subtracting background and autocorrelation terms, can be received and simply given by the following equation $$I(x,k) = \int_{-\infty}^{\infty} R(k) A(x,k,z) \cos(2kz) dz \quad (4)$$

where x is the transverse position of focus beam spot on the sample along the fast scan axis, k is the wavenumber, $I(x,k)$ is the light intensity, $R(k)$ is the amplitude of light reflected from the reference arm, $A(x,k,z)$ is the amplitude of the light backscattered from the sample, and z is the optical delay mismatch between the sample reflections and the reference reflection in the free space equivalent.

At 504, overlapping filters (M) covering the entire spectrum can be created. Additionally, at 506, band pass filtering along k can be conducted. Collectively, creating overlapping filters 504 and band past filtering 506 can result in creating M spectral bands 507 as depicted in FIG. 7 (e.g., as described in creating M spectral bands 404 in method 400 of FIG. 4). Following along with the example provided above of the spectral interference signal represented by equation (4), the Gaussian shape above the 2D interferogram $I(x,k)$ (e.g., 2D interferogram 605 of FIG. 6) can be used to express the received interferometric fringe at one position. The bandwidth of this full-spectrum fringe can first be defined, and then a filter bank created to divide this full-spectrum fringe into different bands (e.g., creating overlapping filters (M) 504 of method 500). The specifications of this filter bank can depend on several factors, including, but not limited to, 1) filter type, 2) bandwidth of each filter, 3) overlap between different bands, and 4) number of bands. In one exemplary embodiment, a Gaussian filter can be introduced whose function was defined by the following equation:

$$G(n) = \exp\left[-\frac{(n-m)^2}{2\sigma^2}\right] \quad (5)$$

where n is the spectral element number that varies from 1 to 1400 and is linearly mapped to wavenumber k. The range of sampled k can be 10000 to 9091 cm$^{-1}$, corresponding to a wavelength range of 1000 to 1100 nm. The bandwidth, referred to as "BW," (e.g., as depicted in 604 of FIG. 6) of the full spectrum can be 69 nm, which can provide a FWHM axial spatial resolution of 5.3 µm. m is the position of the spectral peak. In an exemplary embodiment, the peaks of the spectral Gaussian filters can be placed at 9784, 9625, 9466, and 9307 cm$^{-1}$. $\sigma^2$ is the variance of the Gaussian filter in terms of the number of spectral elements. In an exemplary embodiment, the FWHM amplitude bandwidth, referred to as "bw," of the bandpass filters can equal to $2\sqrt{2\ln 2}\sigma$, covering 378 spectral elements, corresponding to a wavelength range of 27 nm or a wavenumber range of 245 cm$^{-1}$.

The four (4) bandpass filters (e.g., as depicted in 608, 610, 612, and 614 of FIG. 6), described in such an exemplary embodiment, can overlap so that none of the frequency components of the original signal are lost in the processing. FIG. 6 visually displays a 2D spectral interferogram 605 split at 606 (e.g., via 404 of method 400 of FIG. 4) into four new spectra with smaller k bandwidth, with "BW" 604 indicating the bandwidth of a full-spectrum filter and multiple "bw"s 608, 610, 612, and 614 being the bandwidth of multiple Guassian filters, respectively, and regions of non-zero values in the data block are indicated by the dark shaded patterns 616, 618, 620, and 622 (similarly visually depicted, for example in FIG. 7).

At 508, the M spectral bands 507 from each individual frequency band can be passed into conventional Fourier-domain OCT algorithms to Fourier transform along k. Additionally, phase information can be dropped to result in amplitude information for each spectral band 509 (e.g., as depicted in FIG. 7). For example, the OCT signals therefore can be directly calculated from the decomposed interferograms I'(x,k) by applying Fourier transform upon wavenumber k. The computed OCT signal can be a complex function, Ĩ(x,z), which can be written as the following equation:

$$\tilde{I}(x,z) = FFT\{I'(x,k)\} = A(x,z)\exp[i\varphi(x,z)] \quad (6)$$

where $\varphi(x,z)$ is the phase of the analytic signal $\tilde{I}(x,z)$. The amplitudes of the OCT signals, A(x,z), can be used while the phase information can be selectively disregarded.

At 510, a fixed value can be set for removal of high decorrelation generated by background noise. Decorrelation of OCT signal amplitude between B-scans taken at the same nominal position can be caused by several sources: (1) flow, (2) bulk tissue motion or scanner position error, and (3) background noise. To help accentuate true flow measurement in the images created and improve the signal-to-noise ratio for flow detection, removal of high decorrelation generated by background noise is desirable. Background noise is random and therefore has high decorrelation between B-scan frames. Noise predominates in pixels with low OCT signal amplitude and therefore flow cannot be assessed in these pixels with any accuracy. A fixed decorrelation value of zero (0) can be assigned to these pixels with low OCT signal amplitude. For example, this can be achieved by setting the low signal pixels a constant amplitude value. The threshold value, for example, can then be chosen to be two standard deviations above the mean background value measured when the sample beam was blocked.

At 512, decorrelation calculation can be obtained between adjacent amplitude frames. For example, split-spectrum decorrelation 122 as described in FIG. 1 can be utilized to produce decorrelation images for each spectral band 513 (e.g., as depicted in FIG. 7 visually).

At 514, decorrelation images for each spectral band 513 having excessive motion noise can be eliminated. To help accentuate true flow measurement in the images created and improve the signal-to-noise ratio for flow detection, removal of decorrelation generated by bulk tissue motion or scanner position is desirable. Saccadic and micro-saccadic eye movements are rapid and cause a high degree of decorrelation between B-scans, as depicted, for example, in flowchart 800 of FIG. 8. Such movements can be seen in visual 802 which displays three frames of a set of seven (7) decorrelation images 804 (Dn) of the region around the optic nerve head (ONH), computed from eight (8) OCT B-scans at the same Y location. Each decorrelation image frame depicted can be calculated from a pair of adjacent B-scan amplitude frames, for example as described using the methods described above. In six (6) of the seven (7) decorrelation frames, flow pixels could be distinguished from non-flow pixels by their higher decorrelation values. However, in frame D4 806, both flow (vessel) and non-flow (bulk tissue) pixels had high decorrelation values possibly due to rapid eye movement (e.g., saccadic). To detect bulk motion, the median decorrelation value in the highly reflective portion of the imaged tissue structures (between the region noted as 808) can be determined. High bulk motion in frame D4 806 can be detected by high median decorrelation value in pixel histogram analysis 810. Histogram analysis can be performed within a high reflectivity band starting at the retinal inner limiting membrane and spanning 30 pixels below (within region 808 of 802. By comparing the median decorrelation value 814 to a preset threshold 812 (e.g., in one exemplary embodiment the threshold was set at 0.15, two standard deviations above the median decorrelation value), it can be determined that a frame (e.g. frame D4) is a statistical outlier and should be eliminated. Visual 816 depicts the result after the removal of the outlier frame D4.

At 516, the decorrelation images at each spectral band that remain after images with excessive motion noise have been removed can be averaged to create an average decorrelation image for each spectral band, therefore resulting in multiple averaged decorrelation images (i.e., one average decorrelation for each spectral band as visualized in FIG. 7).

At 518, the averaged decorrelation images from M spectral bands are averaged to create one final decorrelation image 410 (e.g., as visualized in FIG. 7 and also described in method 400, step 408 of FIG. 4).

Returning back to flowchart 800 of FIG. 8, after removing frame D4 806 as an outlier, the remaining six (6) decorrelation images can be averaged to produce a cleaned decorrelation image 818 which displays high contrast between flow pixels (e.g., bright area in retinal vessels and choroid) and non-flow dark regions. An uncleaned decorrelation image 820 depicts a final decorrelation image had outlier frame D4 806 remained showing less contrast between flow (vessels) and non-flow (static tissue) pixels compared to the cleaned decorrelation image 818, as evident by the lack of completely dark space between retinal vessels in the peripapillary areas circled at 822 and 824.

Utilizing method 500, a 3D dataset comprising a stack of two hundred (200) corrected average decorrelation cross-sectional images, along with the associated average reflectance images, that together spans 3 mm in the slow transverse scan (Y) direction can be obtained. In some embodiments it may be desirable to separate the 3D data into retinal and choroidal regions with the dividing boundary set at the retina pigment epithelium (RPE). The depth (Z position) of the highly reflective RPE can be identified through the analysis of the reflectance and reflectance gradient profiles in depth. The region above the RPE is the retinal layer and the region below is the choroidal layer. The en face X-Y projection angiograms can then be produced by selecting the maximum decorrelation value along the axial (Z) direction in each layer. In ONH scans, the RPE depth just outside the disc boundary can be used to set an interpolated RPE plane inside the disc.

Figure 9:
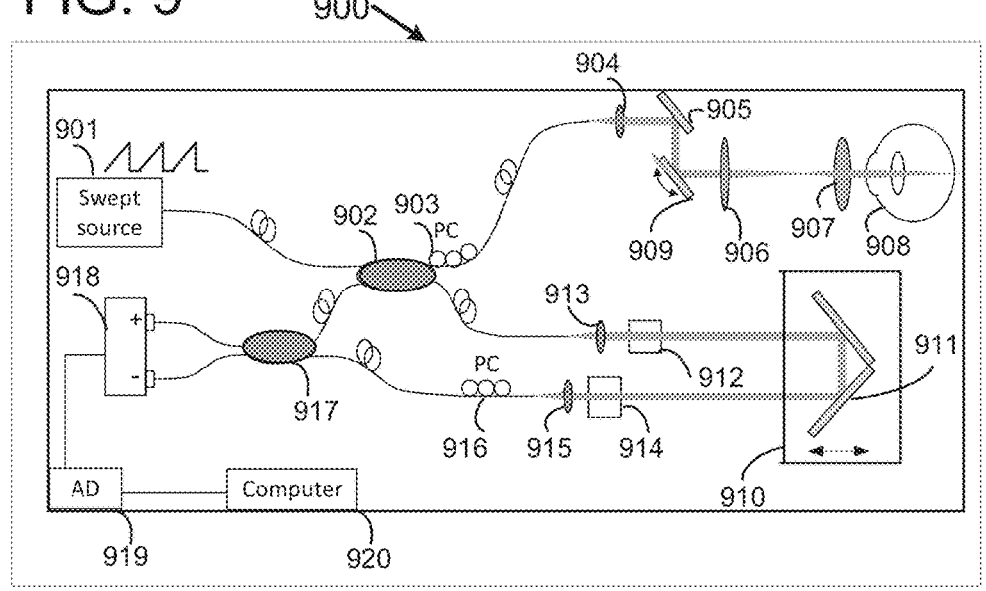
FIG. 9 schematically illustrates an in vivo imaging system for collecting image information.

FIG. 9 schematically illustrates an in vivo imaging system 900 for collecting OCT image information. For example, a high-speed swept-source OCT system 900 (e.g., as described in B. Potsaid, B. Baumann, D. Huang, S. Barry, A. E. Cable, J. S. Schuman, J. S. Duker, and J. G. Fujimoto, "Ultrahigh speed 1050 nm swept source/fourier domain oct retinal and anterior segment imaging at 100,000 to 400,000 axial scans per second," Opt. Express 18(19), 20029-20048 (2010)) can used to demonstrate the methods described above for imaging of microcirculation in the human ocular fundus. High speed swept-source OCT system 900 comprises a tunable laser 901. For example, tunable laser 901 (e.g., a tunable laser from Axsun Technologies, Inc, Billerica, Mass., USA) may have a wavelength of 1050 nm with 100 nm tuning range, a tuning cycle with a repetition rate of 100 kHz and a duty cycle of 50%. Such OCT system 900 can produce a measured axial resolution of 5.3 µm (full-width-half-maximum amplitude profile) and an imaging range of 2.9 mm in tissue. Light from swept source 901 can be coupled into a two by two fiber coupler 902 through single mode optical fiber. One portion of the light (e.g., 70%) can proceed to the sample arm (i.e., the patient interface), and the other portion of the light (e.g., 30%) can proceed to the reference arm.

In the sample arm, a sample arm polarization control unit 903 can be used to adjust light polarization state. The exit light from the fiber coupler 902 can then be coupled with a retinal scanner whereby the light is collimated by sample arm collimating lens 904 and reflected by mirror 905 and two dimensional galvo scanner 909 (e.g., an XY galvonanometer scanner). Two lenses, first lense 906 (e.g., an objective lense) and second lense 907 (e.g., an ocular lense) can relay probe beam reflected by galvo scanner 909 into a human eye 908. For example, a focused spot diameter of 18 µm (full-width-half-maximum amplitude profile) can be calculated on the retinal plane based on an eye model. The average light power (i.e., output power of the laser) onto a human eye can be 1.9 mW, which is consistent with safe ocular exposure limit set by the American National Standard Institute (ANSI).

The reference arm can comprise a first reference arm collimating lens 913, a water cell 912, a retro-reflector 911, a glass plate 914 and a second reference arm collimating lens 915. Glass plate 914 can be used to balance the dispersion between the OCT sample arm and reference arm. Water cell 912 can be used to compensate the influence of dispersion in the human eye 908. Retro-reflector 911 can be mounted on a translation stage 910 which can be moved to adjust the path length in the reference arm.

Light from the sample and reference arm can interfere at beam splitter 917. A reference arm polarization control unit 916 can be used to adjust the beam polarization state in the reference arm to maximum interference signal. The optical interference signal from beam splitter 917 (e.g., a 50/50 coupler) can be detected by a balanced detector 918 (e.g., a balanced receiver manufactured by Thorlabs, Inc, Newton, N.J., USA), sampled by an analog digital conversion unit 919 (e.g., a high speed digitizer manufactured by Innovative Integration, Inc.) and transferred into computer 920 for processing. For example, computer 920 can be used for storing instructions for, and implementing, the methods described herein. Interference fringes, for example, can be recorded by analog digital conversion unit 919 at 400 MHz with 14-bit resolution, with the acquisition driven by the optical clock output of tunable laser 901. In such an exemplary setup, imaging system 900, sensitivity can be measured with a mirror and neutral density filter at 95 dB, with a sensitivity roll-off of 4.2 dB/mm.

While a swept-source OCT system has been described above, the technology disclosed herein can be applied to any Fourier-domain OCT system. In Fourier-domain OCT systems the reference mirror is kept stationary and the interference between the sample and reference reflections are captured as spectral interferograms, which are processed by Fourier-transform to obtain cross-sectional images. In the spectral OCT implementation of Fourier-domain OCT, a broad band light source is used and the spectral interferogram is captured by a grating or prism-based spectrometer. The spectrometer uses a line camera to detect the spectral interferogram in a simultaneous manner. In the swept-source OCT implementation of Fourier-domain OCT, the light source is a laser that is very rapidly and repetitively tuned across a wide spectrum and the spectral interferogram is captured sequentially. Swept-source OCT can achieve higher speed and the beam can be scanned transversely more rapidly (with less spot overlap between axial scans) without suffering as much signal loss due to fringe washout compared to other Fourier-domain OCT systems. However, a very high speed spectral OCT system could also be utilized with the technology disclosed herein.

Any one of the various embodiments as discussed may be incorporated in combination with multiple rings circular scan Doppler OCT to provide total retinal blood flow (TRBF) measurement for both veins and arteries around the optic disc. Utilizing faster OCT systems, higher velocities of flow in arteries (and veins) can be within detectable range and more circles (e.g., rings) can be scanned within a fraction of the cardiac cycle time. By utilizing a scan pattern of multiple rings (e.g., four (4) or more circular scans) the calculation of vessel curvature and slope relative to the OCT beam axis can be obtained. These calculations can allow for more accurate calculation of Doppler angles in the highly curved segments of retinal vessels as they emerge from the optic head nerve (OHN.) The circles can be closer to the ONH, where the Doppler angles are usually larger, obviating the need for a dual-angle scanning protocol. The OCT beam can then approach at a single angle through the center of an undilated pupil. Each scan can therefore yield a valid TRBD measurement, so fewer scans will be needed. As a vessel can be transected by four (4) or more circular scans, the crossing and branching points can be disregarded (in full or part) in favor of straight sections where flow measurements can be more reliable. With faster scan times per circular scan, motion errors can be reduced as well. In lieu of color disc photography commonly utilized in combination with Doppler OCT, 3D angiography utilizing the techniques discussed (e.g. SSADA) can be used to resolve 3D vessel anatomy.

Figure 10:
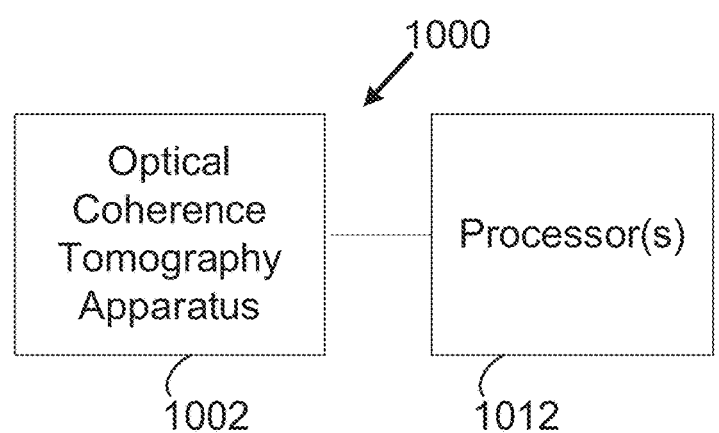
FIG. 10 illustrates an embodiment of an in vivo imaging system in accordance with various embodiments described herein.

Any one or more of various embodiments as discussed may be incorporated, in part or in whole, into a system. FIG. 10 illustrates an exemplary embodiment of an in vivo imaging system (e.g. an OCT system) 1000 in accordance with various embodiments described herein. In the embodiments, OCT system 1000 may comprise an OCT apparatus 1002 and one or more processors 1012 coupled thereto. One or more of the processors 1012 may be adapted to perform methods in accordance with various methods as disclosed herein. In various embodiments, OCT system 1000 may comprise a computing apparatus including, for example, a personal computer in any form, and in various ones of these embodiments, one or more of the processors may be disposed in the computing apparatus. OCT systems in accordance with various embodiments may be adapted to store various information. For instance, an OCT system may be adapted to store parameters and/or instructions for performing one or more methods as disclosed herein.

In various embodiments, an OCT system may be adapted to allow an operator to perform various tasks. For example, an OCT system may be adapted to allow an operator to configure and/or launch various ones of the above-described methods. In some embodiments, an OCT system may be adapted to generate, or cause to be generated, reports of various information including, for example, reports of the results of scans run on a sample.

In embodiments of OCT systems comprising a display device, data and/or other information may be displayed for an operator. In embodiments, a display device may be adapted to receive an input (e.g., by a touch screen, actuation of an icon, manipulation of an input device such as a joystick or knob, etc.) and the input may, in some cases, be communicated (actively and/or passively) to one or more processors. In various embodiments, data and/or information may be displayed, and an operator may input information in response thereto.

Figure 11:
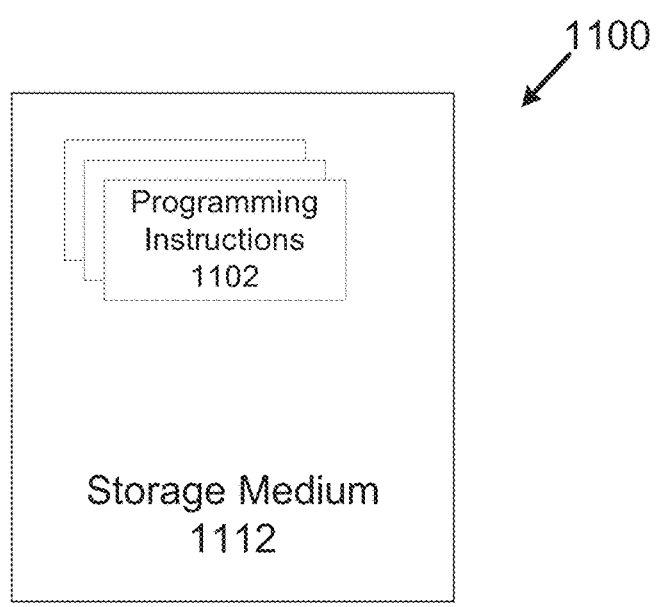
FIG. 11 illustrates an embodiment of an article of manufacture for in vivo imaging in accordance with various embodiments described herein.

Any one or more of various embodiments as discussed may be incorporated, in part or in whole, into an article of manufacture. In various embodiments and as shown in FIG. 11, an article of manufacture 1100 in accordance with various embodiments described herein may comprise a storage medium 1112 and a plurality of programming instructions 1102 stored in storage medium 1112. In various ones of these embodiments, programming instructions 1102 may be adapted to program an apparatus to enable the apparatus to perform one or more of the previously-discussed methods.

In various embodiments, an OCT image may provide data from which a diagnosis and/or evaluation may be made. In embodiments, such determinations may relate to biologic tissue structure, vasculature, and/or microcirculation. For example, in some embodiments, 3-D in vivo imaging of a biologic tissue and quantifying flow of blood through individual vessels therein may be useful in understanding mechanisms behind a number of disease developments and treatments including, for example, ischemia, degeneration, trauma, seizures, and various other neurological diseases. In still other embodiments, an OCT image and techniques herein disclosed may be used to identify cancer, tumors, dementia, and ophthalmologic diseases/conditions (including, e.g., glaucoma, diabetic retinopathy, age-related macular degeneration). Still further, in various embodiments, OCT techniques as herein disclosed may be used for endoscopic imaging or other internal medicine applications. The foregoing illustrative embodiments of diagnosis and/or evaluation are exemplary and thus embodiments described herein are not limited to the embodiments discussed.

Although certain embodiments have been illustrated and described herein for purposes of description, it will be appreciated by those of ordinary skill in the art that a wide variety of alternate and/or equivalent embodiments or implementations calculated to achieve the same purposes may be substituted for the embodiments shown and described. Those with skill in the art will readily appreciate that embodiments described herein may be implemented in a very wide variety of ways.

EXEMPLARY EMBODIMENTS

A. Certain Embodiments

Macular and ONH imaging were performed on three normal volunteers using a swept-source OCT system 900 described herein, as approved by an Institutional Review Board (IRB). For each imaging, the subject's head was stabilized by chin and forehead rests. A flashing internal fixation target was projected by an attenuated pico projector using digital light processing (DLP) technology (Texas Instruments, Dallas, Tex., USA). The imaging area on the fundus was visualized by the operator using real-time en face view of a 3 mm×3 mm OCT preview scan.

The swept-source OCT system was operated at 100-kHz axial scan repetition rate. In the fast transverse scan (X) direction, the B-scan consisted of 200 A-scans over 3 mm. In the slow transverse scan (Y) direction, there were 200 discrete sampling planes over 3 mm. Eight consecutive B-scans were acquired at each Y position. This is referred to as the "M-B-scan mode" (e.g., as illustrated in FIG. 3) because it enables detection of motion between consecutive B-scans at the same position. Thus, it took 3.2 sec to obtain a 3D volumetric data cube comprised of 1600 B-scans and 32,0000 A-scans. Under this scanning protocol, methods described herein were applied to the repeated frame sequences at each step. Finally, the 200 calculated B-scan frames were combined to form 3D blood perfusion images of posterior part of the human eye.

Figure 12:
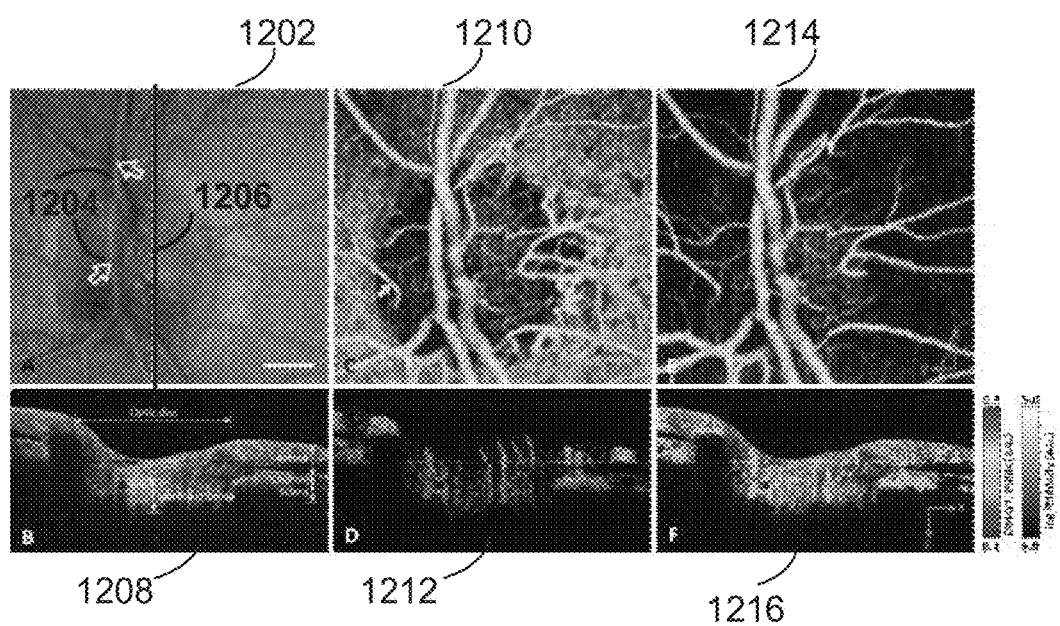
FIG. 12 illustrates in vivo 3-D volumetric structure images of the optic nerve head using imaging methods in accordance with various embodiments described herein.

FIG. 12 illustrates in vivo 3-D volumetric structure images (3.0 (x)×3.0 (y)×2.9 (z) mm) of the optic nerve head (ONH) in the right eye of a myopic individual using imaging methods in accordance with various embodiments described herein. From one 3D volumetric dataset, both reflectance intensity images and decorrelation (angiography) images were obtained. For the optical nerve head (ONH) scan, the en face maximum projection of reflectance intensity 1202 showed the major retinal blood vessels and the second order branches 1204, but finer branches and the microcirculation of the retina, choroid, and optic disc were not visible. In the vertical cross-sectional intensity image 1208 taken from plane 1206 of projection 1202, the connective tissue struts (bright) and pores (dark) of the lamina cribosa could be visualized deep within the optic disc. Around the disc, the retina, choroid, and sclera can be delineated. The ONH angiogram obtained by the methods described herein showed both many orders of vascular branching as well as the microcirculatory network. The en face maximum decorrelation projection angiogram 1210 showed many orders of branching from the central retinal artery and vein, a dense capillary network in the disc, a cilioretinal artery (reference by an arrow in angiogram 1210 at the nasal disc margin), and a near continuous sheet of choroidal vessels around the disc, much of which could not be visualized well on the en face intensity image 1202. The vertical SSADA cross-section decorrelation image 1212 (in the same plane 1206 as 1208 displayed) created showed blood flow in blood vessels in the disc (represented by arrows), retinal vessels, and choroid that form columns from the surface to a depth of ~1.0 mm. It may be unclear if this represents deep penetrating vessels or if this is represents decorrelation projection artifact. Projection artifact refers to the fact that light reflected from deeper static structures may show decorrelation due to passing through a more superficial blood vessel. This type of artifact is evident where the peripapillary retinal vessels seem thicker than they should be, for example in fly-through movie still frame image 1216 and in decorrelation image 1212. Due to this artifact, these vessels extended down the full depth of the nerve fiber layer (NFL), and the decorrelation signal appeared in the subjacent pigment epithelium (RPE), which should be avascular.

To separately view the retinal vessels and superficial disc vessels, pixels were removed below the level of the peripapillary RPE to remove the choroid. The resulting en face angiogram 1214 showed that the superficial vascular network nourishes the disc ends at the disc boundary. By comparison, the choroidal circulation formed an almost continuous sheet of blood flow under the retina as shown in 1210. The en face images 1202, 1210, and 1214 show RPE atrophy in a temporal crescent just outside the disc margin. Inside the crescent there was also a small region of choriocapillaris atrophy (see the arrow region within 1210). Overlaying the cross-sectional gray scale reflectance intensity image with the color scale flow (decorrelation) image showed that the major retinal branches vessels were at the level of the peripapillary NFL, as shown in fly-through movie still frame image 1216 (i.e., how the disc, retina, and choroid are perfused in a 3D volumetric fashion). It also showed the blood flow within the full thickness of the choroid. The combined image 1216 also showed that the deeper disc circulation resides primarily in the pores of the lamina cribosa and not in the connective tissue struts. This may be the first time that the disc microcirculation has been visualized noninvasively in such a comprehensive manner. The horizontal line across the image was a result of a fixed pattern artifact that originated from the swept laser source.

Another exemplary embodiment disclosed herein was demonstrated in macular angiography. The macular region of the fundus is responsible for central vision. Capillary dropout in the macular region due to diabetic retinopathy is a major cause of vision loss. Focal loss of the choriocapillaris is a possible causative factor in the pathogenesis of both dry and wet age-related macular degeneration, the leading cause of blindness in industrialized nations. Thus macular angiography is important. The technology described herein was used to demonstrate macular angiography of both the retinal and choroidal circulations in a normal eye as shown in the in vivo 3-D volumetric structure images (3.0 (x)×3.0 (y)×2.9 (z) mm) of the macula in FIG. 13.

The vascular pattern and capillary networks visualized using the technology disclosed herein were similar to those previously reported using phase-based OCT angiography techniques. The flow pixels formed a continuous microcirculatory network in the retina. There was an absence of vascular network in the foveal avascular zone (as shown in en face maximum decorrelation projection angiogram 1302) of approximately 600 μm diameter, in agreement with known anatomy. There were some disconnected apparent flow pixels within the foveal avascular zone due to noise. Horizontal OCT cross section through the foveal center (upper dashed line in 1302) with merged flow information (decorrelation represented in bright/color scale) and structure information (reflectance intensity represented in gray/darker scale) is represented with foveal center image 1304. Inspection of foveal center image 1304 shows these false flow pixels to be decorrelation noise in the high reflectance layers of the RPE and photoreceptors. The choriocapillaris layer forms a confluent overlapping plexus, so it is to be expected that the projection image of the choroid circulation (see en face maximum decorrelation projection angiogram of the choroidal circulation 1306) shows confluent flow. Similar to 1304, a merged horizontal OCT cross section of the inferior macula (lower dashed line in 1302) is represented with inferior macula image 1308. The cross section images 1304 and 1308 showed retinal vessels from the NFL to the outer plexiform layer, in agreement with known anatomy. The flow in the inner choroid had higher velocity as based on decorrelation seen in the bright/color scale. The volume was also greater than the retinal circulation (as shown in the cross section images 1304 and 1308), again consistent with known physiology that the choroidal circulation has much higher flow than the retinal circulation. There were signal voids in the outer choroid which may be due to fringe washout from high flow velocity and the shadowing effect of overlying tissue. The cross section images 1304 and 1308 also showed a few spots of decorrelation in the RPE layer. These are likely artifacts because the RPE is known to be avascular. As mentioned previously, this is likely due to the projection of decorrelation of flow in a proximal layer (i.e., inner retinal layers) onto distal layers with a strong reflected signal (i.e., RPE). There was also a tendency for vessels to form vertical arrays in the inner retina, which may in some instances be due to the projection artifact as well.

Another embodiment disclosed herein was demonstrated to appreciate the differences between full-spectrum, pixel-averaging, and split-spectrum techniques (as described in FIG. 1) for decorrelation-based angiography. To obtain angiograms, the methods described above were used, in particular with reference to FIG. 1 and as described by equations (1)-(3), respectively. For fair comparison, identical motion error reduction, noise threshold, and en face projection methods were used.

Figure 14:
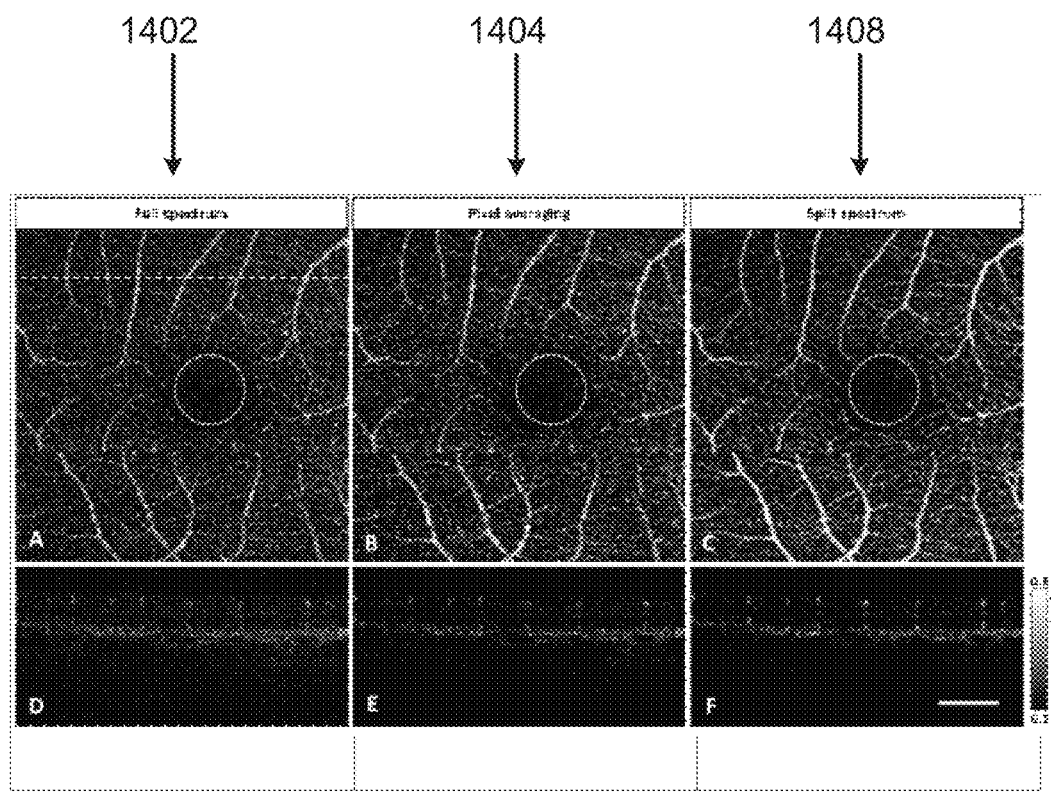
FIG. 14 illustrates in vivo images of macular retinal circulation using methods in accordance with prior art methods and in accordance with various embodiments described herein.

FIG. 14 illustrates en face angiograms of macular retinal circulation using methods in accordance with prior art methods full-spectrum (1402) and pixel-averaging (1404) and in accordance with various embodiments described herein (1408). While the prior art methods and those described herein provided good visualization of major macular vessels, the capillary network looked the cleanest and most continuous in split-spectrum angiogram 108 generated with the split-spectrum embodiment. The pixel-averaging method producing pixel-averaging angiogram 1404 displays the second cleanest and continuous capillary network. The full-spectrum method producing full-spectrum angiogram 1402 showed significantly more disconnected flow pixels that were likely to be noise. The noise can be most easily appreciated in the foveal avascular zone (inside the yellow circles of 1402A, 1402B, and 1408C images of 600-um diameter), which should not have any retinal vessels, including capillaries. In the split-spectrum angiogram 1408, there was a near continuous visualization of the capillary network just outside the avascular zone, while this loop appeared broken up using the other two prior art techniques. The cross-sectional angiograms for each method as displayed in 1402D, 1404E, and 1408F (all scanned across a horizontal dashed line as shown in 1402A showed that the split-spectrum method provided the cleanest contrast between distinct retinal vessels and dark background. Again, the pixel-averaging method was second best, and the full-spectrum method showed visible snow-like background noise.

Figure 15:
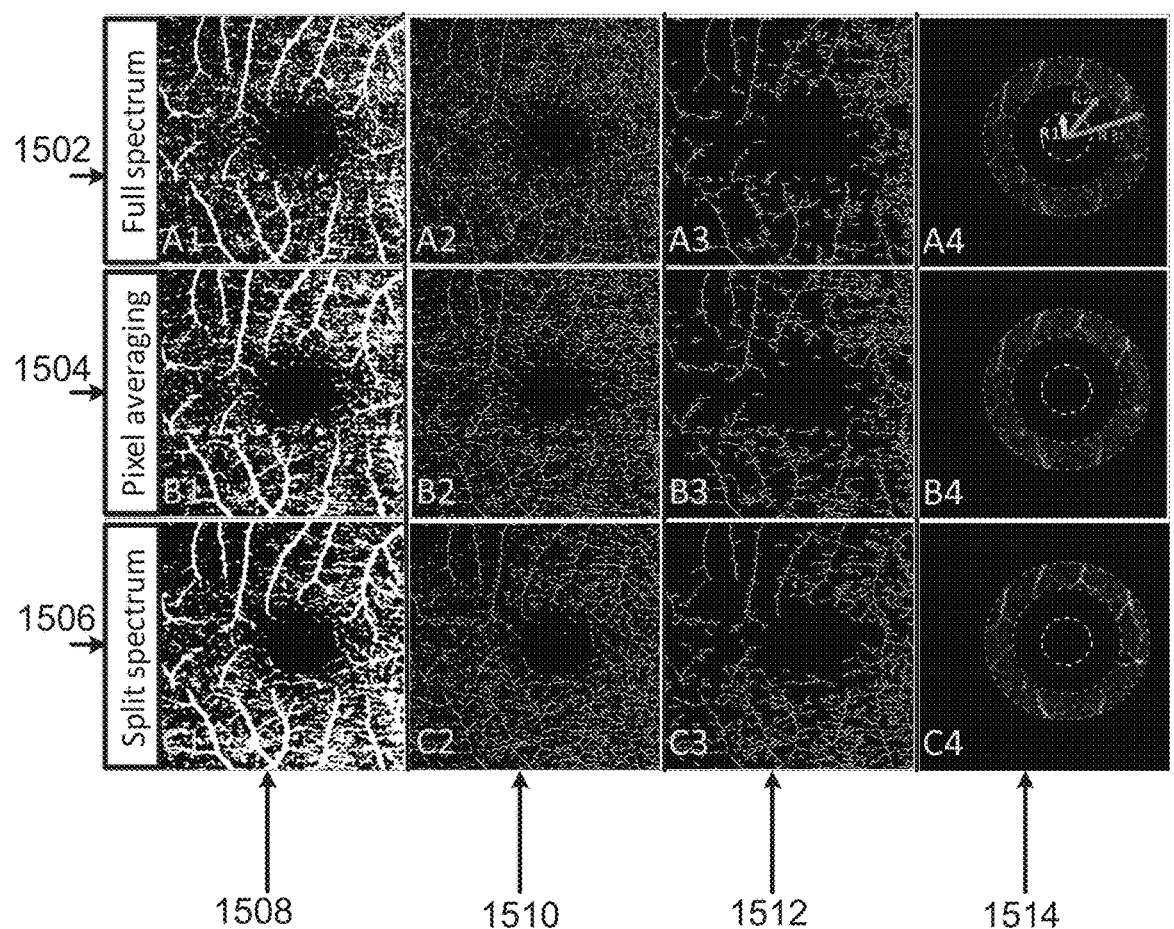
FIG. 15 illustrates in vivo images depicting vascular connectivity and signal to noise ratio (SNR) using methods in accordance with prior art methods and in accordance with various embodiments described herein.

To obtain quantitative figures of merit to compare the three decorrelation-based angiography techniques, two pieces of anatomic knowledge were used. One is that the retinal vessels form a continuous network, and the other is that there are no retinal vessels within the foveal avascular zone. FIG. 15 illustrates in vivo images depicting vascular connectivity and signal to noise ratio (SNR) using methods in accordance with prior art methods and in accordance with various embodiments described herein. In FIG. 15, images 1502A1-1502A4 were obtained using the full-spectrum method (all in row 1502), images 1504B1-1504B4 were obtained using the pixel-averaging method (all in row 1504), and images 1506C1-C4 were obtained using the split-spectrum technology described herein. To assess vessel connectivity, the projection images (1402A, 1404B, and 1408C of FIG. 14) obtained by the three different methods were converted to binary images (e.g., binarized) (as shown in the images in first column 1508 of FIG. 15, images 1502A1, 1504B1, and 1506C1) based on a fixed threshold. Then a skeletonizing morphological operation (e.g., skeletonized) was applied to obtain a vascular network made of 1-pixel wide lines and dots (as shown in the images in second column 1510 of FIG. 15, images 1502A2, 1504B2, and 1506C2). Next the unconnected flow pixels were separated from the connected flow skeleton (e.g., filtered to remove unconnected flow pixels) (as shown in the images in third column 1512 of FIG. 15, images 1502A3, 1504B3, and 1506C3). The vascular connectivity was defined as the ratio of the number of connected flow pixels to the total number of flow pixels on the skeleton map. Connectivity was analyzed on the OCT macular angiograms of six eyes of the three participants (see Table 1 below). A comparison of the three techniques based on paired t-tests showed that the split-spectrum technology had significantly better connectivity relative to the pixel-averaging (p=0.037) and full-spectrum (p=0.014) techniques. The split-spectrum technology disclosed herein reduced the number of unconnected flow pixels (18%) by more than a factor of 2 when compared with the full-spectrum prior art technique (39%).

To compute a signal to noise (SNR) for the decorrelation signal, it was necessary to define relevant signal and noise regions. For the macula, fortuitously, the central foveal avascular zone (FAZ) is devoid of blood vessels, including capillaries. The parafoveal capillary network nourishes the fovea and the loss of these capillaries in diabetic retinopathy is an important mechanism in the loss of vision. Thus the ratio of decorrelation value in the parafoveal region relative to the FAZ can be a clean and clinically relevant way to compute SNR. In the fourth column 1512 of FIG. 15, images 1502A4, 1504B4, and 1506C4, show decorrelation SNR, where the noise region was inside the foveal avascular zone (displayed as inner dotted circles with radius R1) and the signal region was the parafoveal annulus (as displayed the grayed region between radius R2 and radius R3). The radius of the FAZ (R1) is approximately 0.3 mm. Therefore, it was chosen that the central FAZ with a radius of 0.3 mm was the noise region and the annular parafoveal region between 0.65 (R2) and 1.00 mm (R3) radii was the signal region. Therefore, the decorrelation signal-to-noise ratio DSNR can be represent using the following formula:

$$DSNR = \frac{\overline{D}_{Parafovea} - \overline{D}_{FAZ}}{\sqrt{\sigma_{FAZ}^2}} \quad (7)$$

where $\overline{D}_{Parafovea}$ and $\overline{D}_{FAZ}$ are the average decorrelation values within the parafoveal annulus and FAZ, respectively; and $\sigma_{FAZ}^2$ is the variance of decorrelation values within the FAZ. These computations were performed over the en face maximum projection images.

The DSNR was analyzed on the OCT macular angiograms performed on six eyes of the three participants (see Table 1 below). The paired t-test showed that the DSNR of the split-spectrum technology was significantly higher than the pixel-averaging technique (p=0.034) and the full-spectrum technique (p=0.012). The split-spectrum technology improved the DSNR by more than a factor of 2 compared to the full-spectrum technique.

TABLE 1

Vascular Connectivity and Signal-to-Noise Ratio of Three Angiography Algorithms

| Amplitude decorrelation | Connectivity (mean ± sd) | Improvement of connectivity | DSNR (mean ± sd) | Improvement of DSNR |
|---|---|---|---|---|
| full-spectrum | 0.61 ± 0.08 | N/A | 3.30 ± 0.81 | N/A |
| pixel-averaging | 0.70 ± 0.06 | 14.8% | 4.57 ± 1.08 | 38.5% |
| split-spectrum | 0.82 ± 0.07 | 34.4% | 6.78 ± 0.82 | 105% |

DSNR = decorrelation signal-to-noise ratio. Statistical analysis is based on 6 eyes of 3 normal human subjects.

Utilizing the technology disclosed, visualization of both larger blood vessels and the capillary network in the retinal and choroidal circulations has been demonstrated. This visualization can also been achieved using Doppler and other phase-based flow detection techniques, however the SSADA (i.e., the split-spectrum) techniques disclosed have several potential advantages over phase-based techniques. Insensitivity to phase noise is one advantage. Another advantage includes the ability to quantify microvascular flow. Because the effective resolution cell is made isotropic (having the same size in X, Y, and Z dimensions, as described in FIG. 2), it is equally sensitive to transverse (X, Y) and axial (Z) flow. This contrasts with all phase-based techniques, which are intrinsically more sensitive to flow in the axial direction over which Doppler shift occurs. Thus utilizing the technology disclosed results in the decorrelation value as a function of the flow velocity regardless of direction. The faster blood particles move across the laser beam, the higher the decorrelation index of the received signals within a velocity range set by the scan parameters. In theory the saturation velocity should be approximately the size of the resolution cell (0.018 mm) divided by the interframe time delay (0.002 sec), or 9 mm/sec. The minimum detectable flow velocity can be determined by the decorrelation noise floor, which can be based on the decorrelation distribution statistics of the non-flow tissue voxels. In this example, the projection view of split-spectrum technology showed the vascular pattern within the macular capillary zone (parafoveal region). This describes that the split-spectrum technology disclosed is able to detect retinal capillary flow, which is within the range of 0.5-2 mm/sec. Calibration of velocity to decorrelation values using in vitro flow phantom experiments can be done to further determine the minimum detectable flow velocity.

Figure 13:
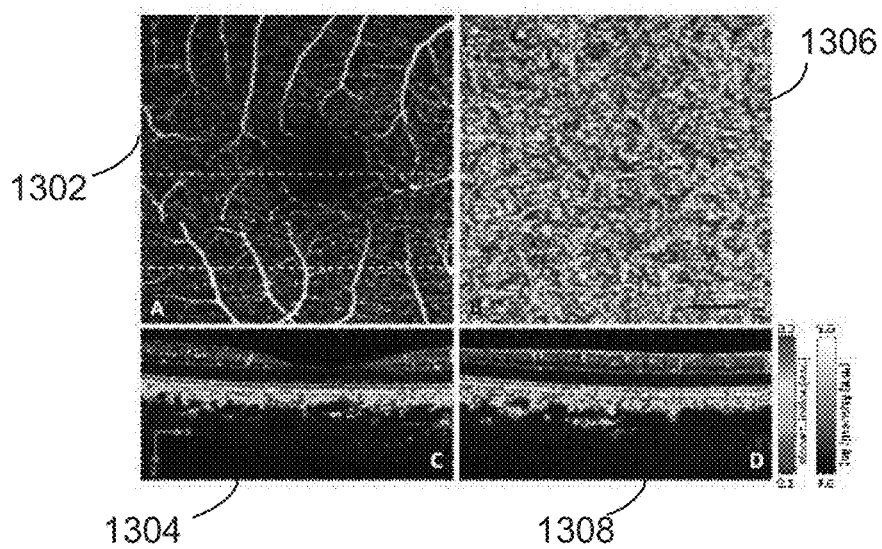
FIG. 13 illustrates in vivo 3-D volumetric structure images of the macula using methods in accordance with various embodiments described herein.

The projection of flow from proximal (shallower) layers to distal (deeper) layers can be challenging. Flow in the major peripapillary retinal arteries and veins (as shown in FIG. 12) and larger macular vessels in the inner retina (as shown in FIG. 13) projects onto the highly reflective RPE, which should not contain any blood vessels. There were also probable projection of flow from the more superficial inner retinal layers (i.e. nerve fiber layer and ganglion cell layer) to the deeper inner retinal layers (i.e. inner and outer plexiform layers). This does not affect the accuracy of en face projection of the retinal circulation, but it could affect the accuracy of cross-sectional angiograms and en face projection of the choroidal circulation. One can raise the threshold decorrelation value for flow identification in deeper voxels if a more superficial voxel has a suprathreshold decorrelation value; however, this can inevitably introduce a potential shadow artifact in place of a flow projection artifact. Thus, images of deeper vessels can be interpreted with this artifact in mind.

Noise from bulk tissue motion, while dramatically reduced using the technology disclosed herein, may not be entirely eliminated. As described in the examples disclosed, no attempt was made to compensate for X-Z motion between consecutive B-scan frames by the use of frame-shift registration. This registration can likely reduce the effect of bulk motion in the X-Z dimensions (though not in the Y direction) and improve the accuracy of flow detection further. It is also apparent from the en face angiograms that there are saccadic motion artifacts in the 3D dataset. This can likely be reduced by the use of 3D registration algorithms.

Figure 16:
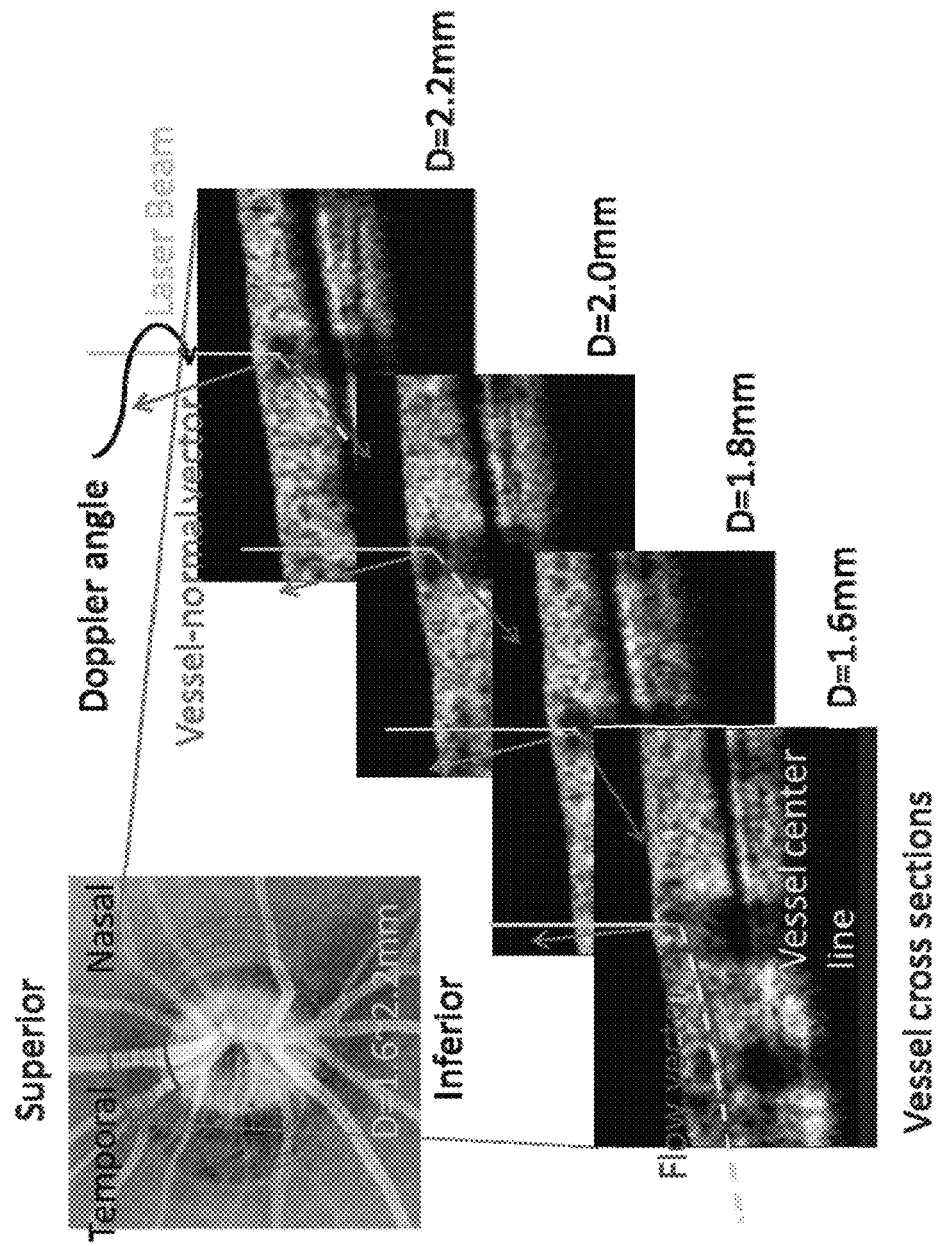
FIG. 16 illustrates in vivo images using methods in accordance with various embodiments described herein, including multiple rings circular scan pattern and Doppler angle estimation for a single vessel.

FIG. 16 illustrates in vivo images using methods in accordance with various embodiments described herein, including a multiple rings circular scan pattern (e.g. a ring number of 4 and a diameter of 1.6-2.2 mm) and Doppler angle estimation for a single vessel. A vessel center line can be constructed based on vessel center position with spline curve fitting. The flow vector at each circle can be estimated using the tangential vector of vessel center line.

The multiple ring circular scan can be done with an ultrahigh-speed OCT. The scan pattern can include multiple concentric circular scans with 4 or more diameters. At each location (e.g., diameter), the circular scan can be repeated to cover the cardiac cycle and reduce the effect of eye movement. The total scan time can cover at least one cardiac cycle. The axial scan density can be high for precise Doppler shift signal calculation.

After the scan is obtained, the vessel location can be detected on each frame for each vessel. For a particular vessel, the center positions on the scans can be used to reconstruct a vessel center line curve. The curve can be used to estimate the Doppler angle between OCT beam and vessel normal vector (as shown FIG. 16). The angle θ can be calculated between the OCT beam and the flow vector, which is the tangential vector of the vessel center line at vessel center. Then, the Doppler angle can be estimated as 90−θ.

With the angle and Doppler shift signal, the blood flow can be estimated by the following equation, $$\text{Flow} = \frac{1}{n} \sum_{i=1}^{n} \iint_{vessel\ area} \frac{\lambda \Delta f_i dxdz}{2n\sin(\alpha_L)} \quad (8)$$

where, λ: is center wavelength of the OCT laser source, $\Delta f_i$ is Doppler shift signal in ith circular scan, n is refractive index, α is Doppler angle on ith circular scan, which is equal to 90−θ, θ is the angle between vessel vector and OCT beam on ith circular scan. When the Doppler angle is close to 0, it can be difficult to detect the vessel position automatically. To solve this problem, an OCT angiography scan can be added into the multiple ring circular scan. For each position (diameter), except the single circular scan which creates Doppler OCT image, multiple circular scans with less axial-scan density can be done just before or after the Doppler scan and the angiography techniques described herein (e.g., SSADA) can be applied to get the OCT angiograph. The Doppler scan and angiography scan can be registered, as they are done at the same location, and eye movement should be small in such short period (<0.1 seconds). Then, vessel positions and regions detected on the angiograph scan can be mapped to the Doppler scan.

In order to get precise flow vector estimation, the interval of circle diameter can be reduced. This can involve increasing the number of circles and therefore the total scan time would increase. In clinical practice, the total scan time is desired to be about 2 seconds. Therefore there is a compromise between scan time and the accuracy of angle estimation in multiple ring circular scanning. To solve this problem, flow vector from a 3D OCT angiograph can be obtained. The 3D angiograph scan can cover the Doppler scan area. The vessel position can be manually or automatically detected on the 3D angiograph and the 3D vessel structure around the optic disc can be reconstructed. The circular Doppler scan and/or circular angiograph scan can be registered to the 3D angiograph scan. An automatic rigid registration based on the vessel pattern and inner limited membrane can be utilized. After the registration, the 3D vessel structure can be mapped to the Doppler scan for vessel detection and angle estimation.

Figure 17:
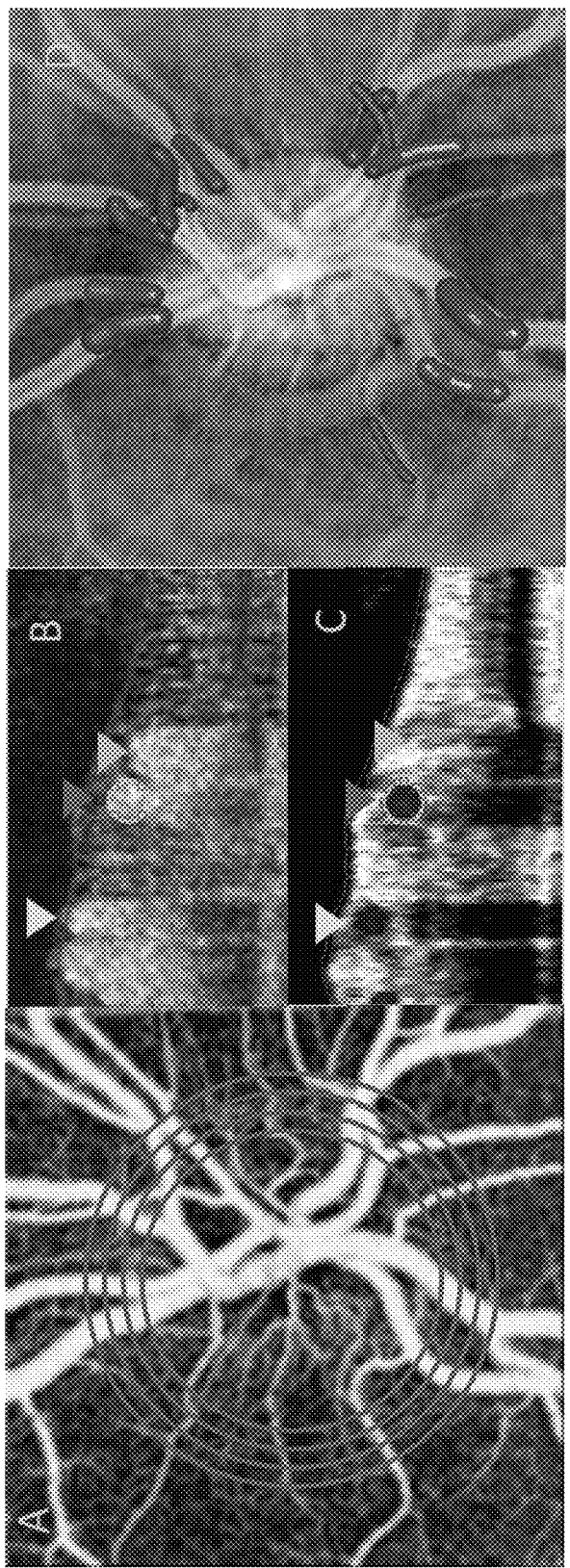
FIGS. 17A-D illustrates in vivo images using methods in accordance with various embodiments described herein, including multiple rings circular scan Doppler OCT in combination with SSADA to provide total retinal blood flow (TRBF) measurement.

For example, on a swept-source OCT with 100,000 ascan/second scan rate, a four ring circular scan pattern was implemented. The scan diameter utilized was 2.2 mm, 2.0 mm, 1.8 mm and 1.6 mm. 8 fast circular scans (500 A scans) followed by 1 slow circular scan (4000 A scans) were scanned on each diameter. Then the scans on 4 diameters were repeated 6 times. Together, the scans took about 2 seconds, within the desired clinical timeframe. The faster scans were used to calculate the OCT angiograph and the slow scan was used to calculate the Doppler shift signal. A 3×3 mm 3D OCT angiography was also obtained. FIGS. 17A-D illustrates in vivo images using methods in accordance with various embodiments described herein, including multiple rings circular scan Doppler OCT in combination with SSADA to provide total retinal blood flow (TRBF) measurement as mentioned above. The multiple ring circular scan was used to calculate the total retinal blood flow around the optic disc using information from both arteries and veins. FIG. 17A shows an en face OCT angiogram computed with the SSADA technology disclosed herein. The vascular pattern, including branching and crossing, can be extracted using a graph search technique. FIG. 17B shows a cross-section SSADA angiogram providing precise positions of the top boundary of retinal vessels (depicted with arrow heads.) FIG. 17C shows a color Doppler display of a section of a circular scan showing the blue and red Doppler shifts in lumen cross-section that can be used for velocity calculations. One vessel (as noted with a green arrowhead) is visible on decorrelation-based angiography image shown in FIG. 17B, but is not on the color Doppler image shown in FIG. 17C. This visualizes decorrelation angiography reliably defining vessel anatomy, while Doppler shift can provide more quantitative velocity information. FIG. 17D shows a composite image showing Doppler measurements (blue & red vessel segments) from the circular scans overlaid on the en face summation view of the 3D OCT scan. This visualization shows that the vessel trajectory (e.g., position, slope, and curvature fit by second order spline function) branching, and crossing can be characterized by the combination of multi-circular and 3D scans, thereby allowing for accurate measurement of TRBF (e.g., by summing flow measurements in arteries and veins in a region and dividing by half.)

B. Additional Embodiments

Certain embodiments are directed to novel quantitative systems for measuring ocular blood flow as described below.

Specifically, these systems are able to measure circulation in ONH (e.g. whole disc/temporal ellipse, peripapillary retina, peripapillary choroid) and macula (e.g. macular retina, macular choroid, fovea avascular zone and the area of non-perfusion). Quantification of different circulation obtained from glaucoma patients compared with that from normal subjects is herein described.

Acquisition of 3D Decorrelation Image

Design of 3D Scan Pattern

Figure 18:
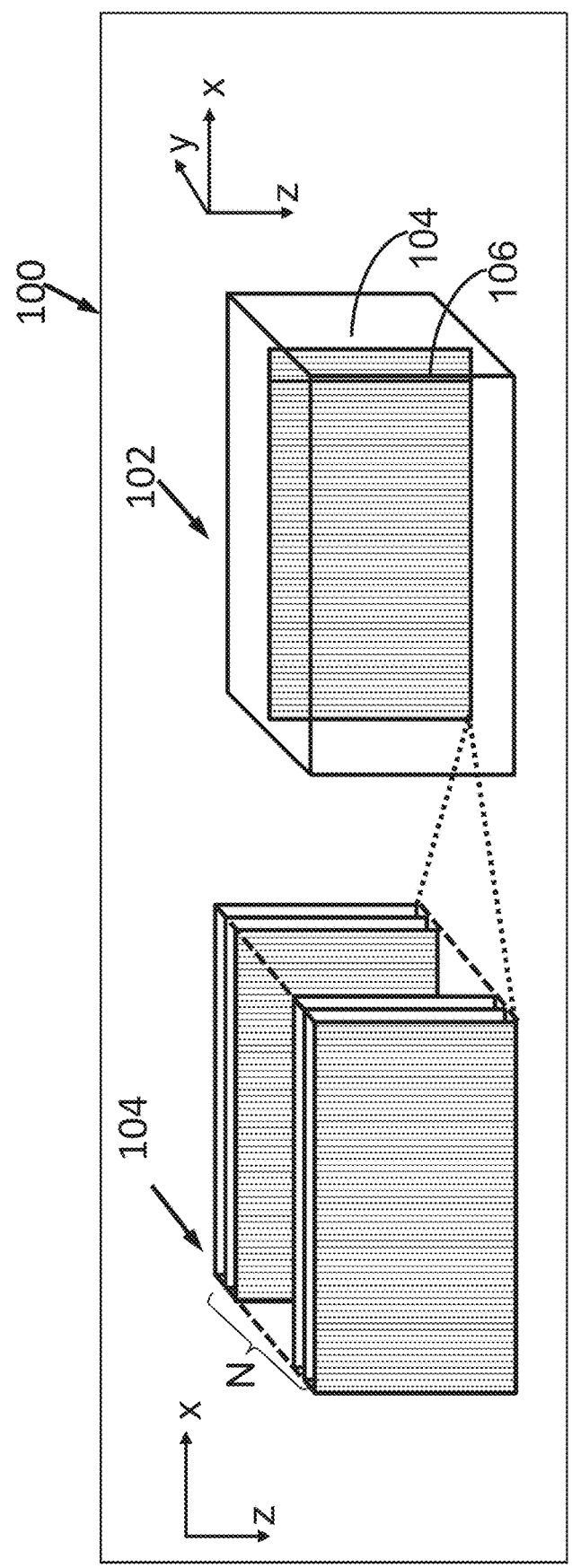
FIG. 18 schematically illustrates an OCT angiography scan pattern for blood flow quantification.

The 3D scan pattern 100 to scan macula and disc of the eye is optimized to implement split-spectrum amplitude decorrelation algorithm (SSADA) [Jia et al., *Opt. Express* 20:4710-4725 (2012)]. It is illustrated in FIG. 18. For each 3D volumetric data 102 comprising data obtained via an M-B-scan mode from an OCT system. M-B-scan 104 is composed by N consecutive B-scans at a single Y position (e.g. N=8). Therefore, for each 3D volumetric data 102, in the fast scan axis, a single B-scan comprises a number of A-scans 106, and in the slow scan axis, there are a number of M-B-scans 104 comprising N consecutive B-scans. For example, the scan pattern used for an OCT system with a scan speed of 100K axial scan/second can contain 200 A-lines covering 3 mm along fast scan direction, and contain 200 M-B-scans (N=8) along slow scan direction. One 3D data set 102 can be acquired in 3.4 seconds. The repeated B-frames 104 are used for the SSADA calculation to obtain both the structure and blood flow images.

Application of SSADA

Figure 19:
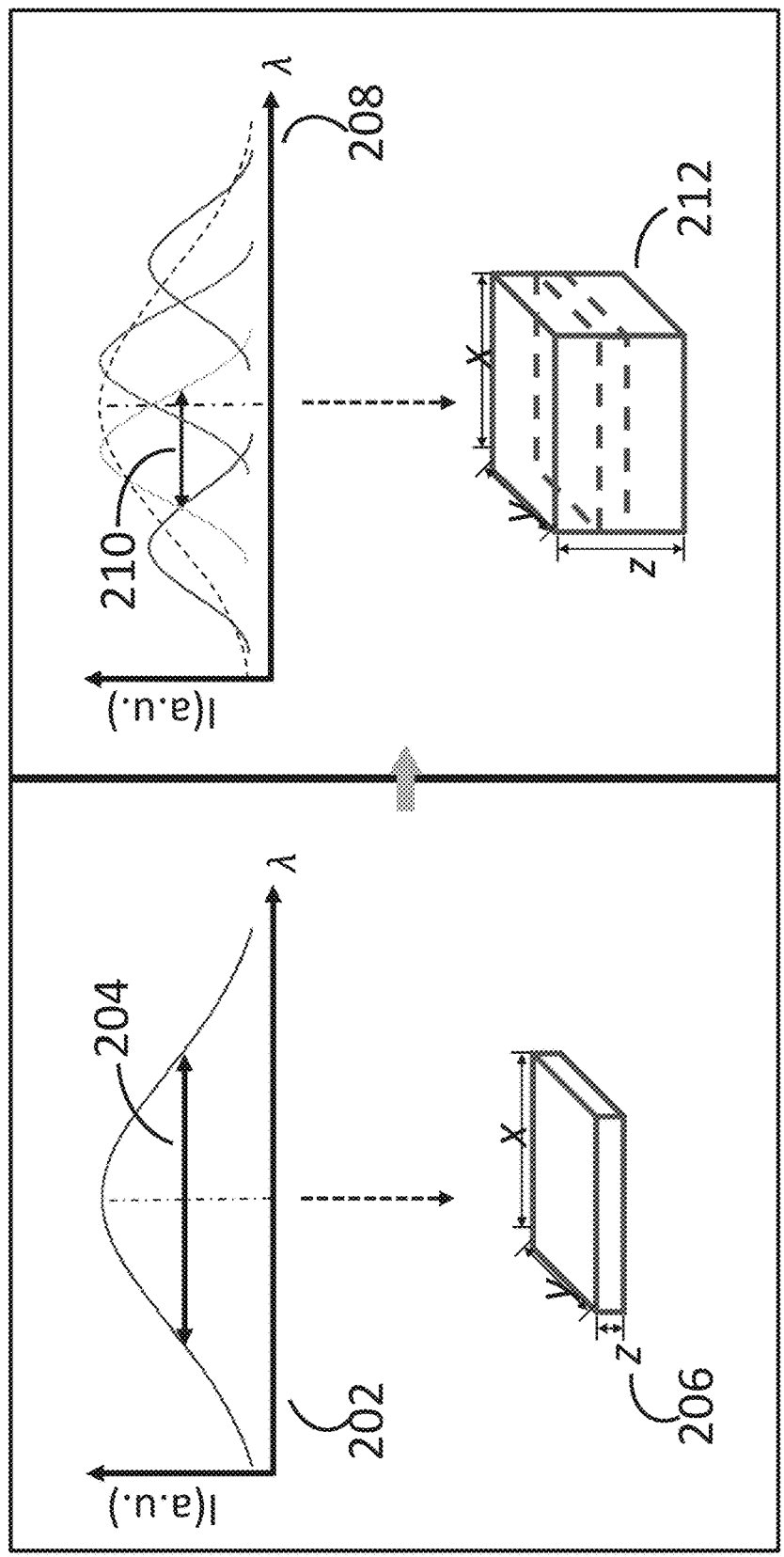
FIG. 19 schematically shows the creation of an isotropic resolution cell.

As described previously [Jia et al., *Opt. Express* 20:4710-4725 (2012)], SSADA can split the spectrum into different frequency bands and calculate decorrelation in each band separately (FIG. 19). The decorrelation (flow) images from the multiple spectral bands can then be averaged together to make full use of the speckle information in the entire OCT spectrum. By splitting the full OCT spectral interferograms into several wavenumber bands, the OCT resolution cell in each band is modified intentionally and less susceptible to axial motion noise.

For visualization purposes, the modified resolution cell is unnecessary to be exactly isotropic; however, for quantification purposes, the isotropic resolution cell is the key point because it can be sensitive to axial and transverse flow equally. In other words, decorrelation value derived from isotropic resolution cell is proportional to velocity regardless of direction. FIG. 19 is an example to explain how to split raw interference spectrum 202 and create an isotropic resolution cell 212. For a swept source OCT setup, the axial (Z) resolution in the resolution cell 206 is determined by the source central wavelength (1050 nm) and its spectral bandwidth 204 (69 nm); and the lateral (X and Y) resolution is determined by the laser beam profile. Using the full-width-half maximum (FWHM) amplitude profile definition, the axial resolution (5.3 μm) is 3.3 times higher than the lateral resolution (17.7 μm) in the resolution cell 206 where X=Y=3.3Z. In order to create an isotropic resolution cell 212 where X=Y=Z, spectrum should be split into different frequency bands with the new bandwidth 210 of 21 μm (e.g. split-spectrum 208). Please note the overlap between different spectral bands can be increased to further enhance image quality, which might also increase computing time.

Quantitative Blood Flow Assessment

Figure 20:
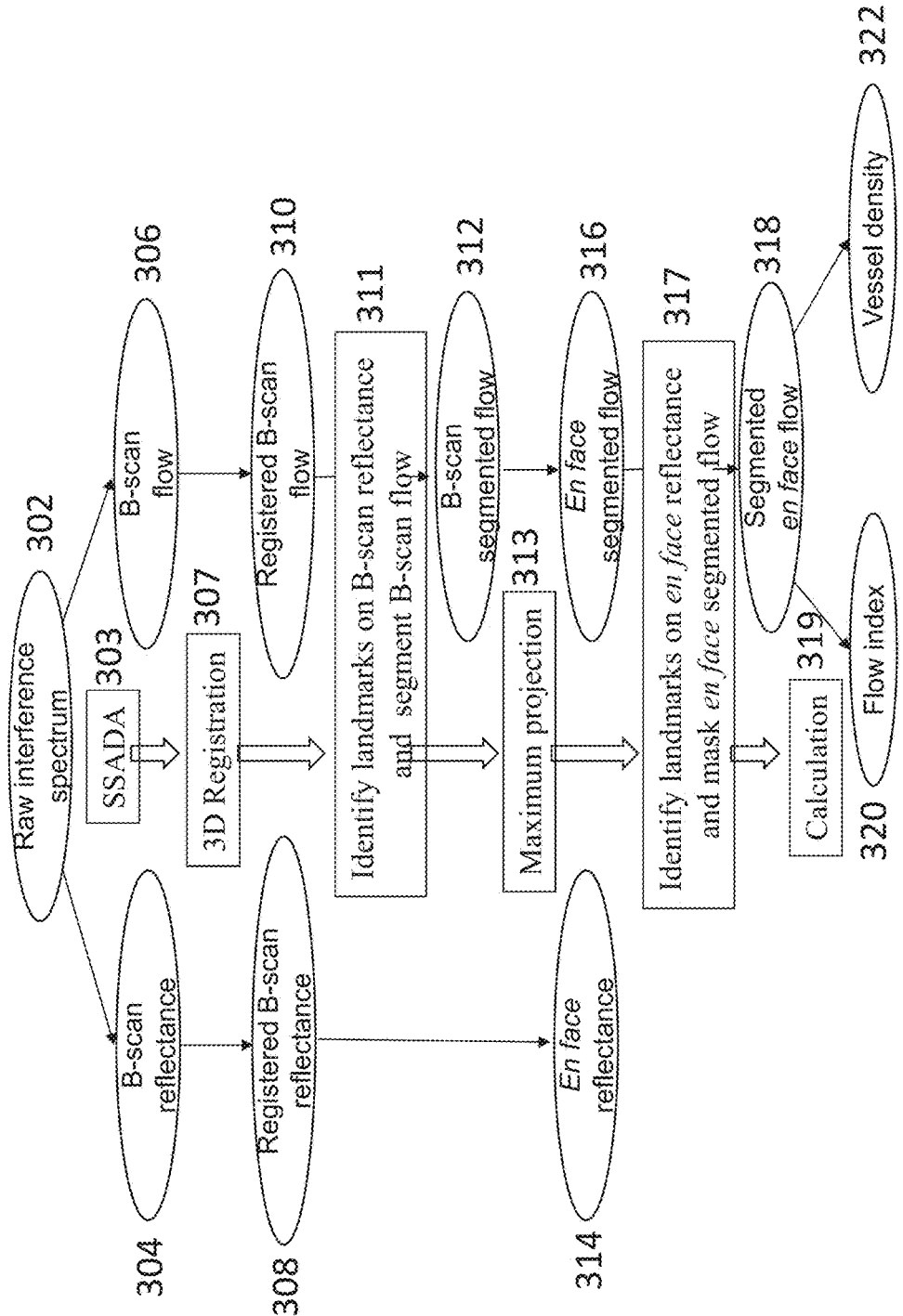
FIG. 20 is a flowchart showing an exemplary method for conducting quantitative blood flow measurements.

A flowchart of quantitative blood flow measurements is provided in FIG. 20. It begins with the detection of measurement flow volumes using reliable anatomical landmarks on reflectance images and ends up with the calculation of two blood flow parameters: flow index and vessel density.

Additionally, the measurement of non-perfusion area is also demonstrated for the quantification purpose.

Detection of Measurement Volumes

Based on the 3D volumetric data set 102 from the above scanning protocol 100, SSADA algorithm 303 is performed on raw interference spectrum 302 and both reflectance intensity images 304 and decorrelation (flow) images 306 can be obtained simultaneously. If necessary, the image distortion due to the saccadic motion artifacts can be reduced by performing 3D registration 307 [Kraus et al., *Biomed. Opt. Express* 3:1182-1199 (2012)]. When registered B-scan reflectance 308 and registered B-scan flow 310 are processed, at 311, the anatomical landmarks are identified on B-scan reflectance 308 and used for the segmentation of B-scan flow 310. At 313, maximum projection algorithm [Jia et al., *Opt. Express* 20:4710-4725 (2012)] is applied on both reflectance 308 and segmented flow 312 image. The projection algorithm finds the maximum reflectance and decorrelation value for each transverse position, representing the highest reflectance and fastest flowing vessel lumen respectively. Next, at 317, the landmarks on en face reflectance 314 are identified and used to mask en face segmented flow image 316. Then segmented en face flow image 318 is obtained and used for calculation of flow index 320 and vessel density 322.

Figure 21:
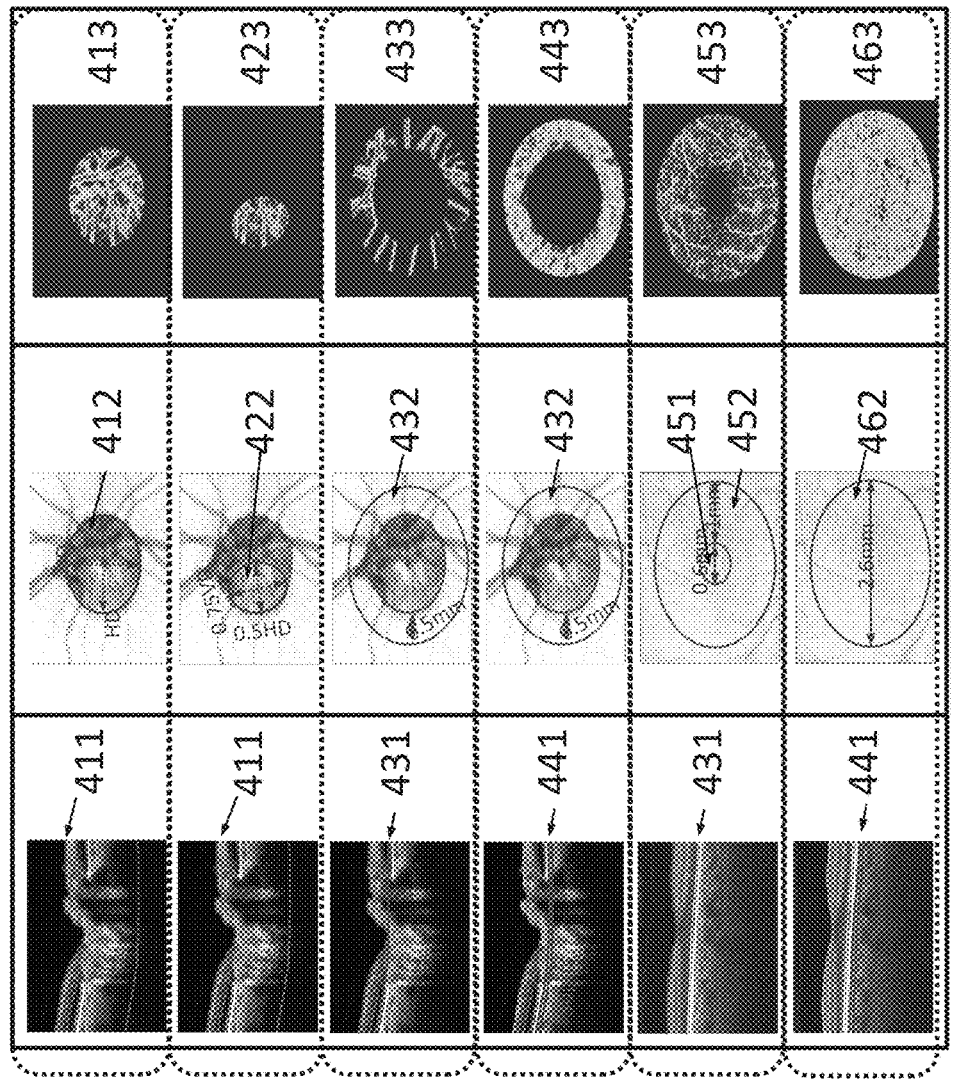
FIG. 21 illustrates the specific segmentation of various ocular vascular beds.

FIG. 21 shows the specific segmentation within various ocular vascular beds, which is also summarized in Table 2 below. At ONH region, segmentation at B-scan for whole disc 410 and temporal ellipse 420 is supplementary data and of lesser value, so all signals between internal limiting membrane (ILM) 411 and bottom can remain. The ellipse bounding neural canal opening (NCO) 412 can be selected for whole disc angiography 413 and ellipse at temporal area (tilted along disc-fovea axis) 422 for temporal ellipse angiography 423. For peripapillary retina 430, the region between ILM 411 and the inner-segment/outer-segment (IS/OS) junction plane 431 is for retina and 0.5 mm wide region surrounding the disc ellipse 432 can be demarcated for peripapillary region. For peripapillary choroid 440, the region between retinal pigment epithelium (RPE) 441 and 50 μm below it is for choroid and peripaillary region is same as defined above. At macula region, macula retina 450 can be separated by segmenting the region between ILM 411 and IS/OS 431 at B-scan and 1 mm wide region 452 surrounding fovea avascular zone (FAZ) 451 at en face flow image to obtain perifovea macular angiography 453; macula choroid 460 can also be extracted by choosing the region between RPE 441 and 50 μm below it at B-scan and a round region 462 centered at FAZ 451.

TABLE 2

Summary of segmentation of various vascular beds

| Vascular beds | Segmentation at B-scan | Segmentation at En face |
|---|---|---|
| ONH - Whole Disc (410) | Between ILM (411) and bottom | Ellipse bounding NCO (412) |
| ONH - Temporal Ellipse (420) | Between ILM (411) and bottom | Ellipse at temporal area (tilted along disc-fovea axis) (422) |
| Peripapillary Retina (430) | Between ILM (411) and IS/OS (431) | 0.5 mm wide region (432) surrounding the disc ellipse (412) |
| Peripapillary Choroid (440) | Between RPE (441) and 50 μm below it | 0.5 mm wide region (432) surrounding the disc ellipse (412) |

TABLE 2-continued

Summary of segmentation of various vascular beds

| Vascular beds | Segmentation at B-scan | Segmentation at En face |
|---|---|---|
| Macular Retina (450) | Between ILM (411) and IS/OS (431) | 1 mm wide region (452) surrounding FAZ (451) (D = 0.6 mm) |
| Macular Choroid (460) | Between RPE (441) and 50 μm below it | Round region (462) (D = 2.6 mm) centered at FAZ (451) |

Dividing boundaries at B-scans can be identified through the analysis of the reflectance gradient profiles in depth. The disc boundary can be identified by detecting the boundary of NCO and the FAZ 451 boundary can be identified by the retina thickness map on the macula on which the thinnest point is the center of FAZ 451 and the circle region with diameter of 600 μm is the size of FAZ 451 [Roh and Weiter, "Retinal and Choroidal Circulation" in *Ophthalmology*, M. Yanoff and J. S. Duker eds. (Mo: Mosby Elsevier, St. Louis, 2008)]. Other boundary detection skills can also be applied for the identification of landmarks.

Figure 22:
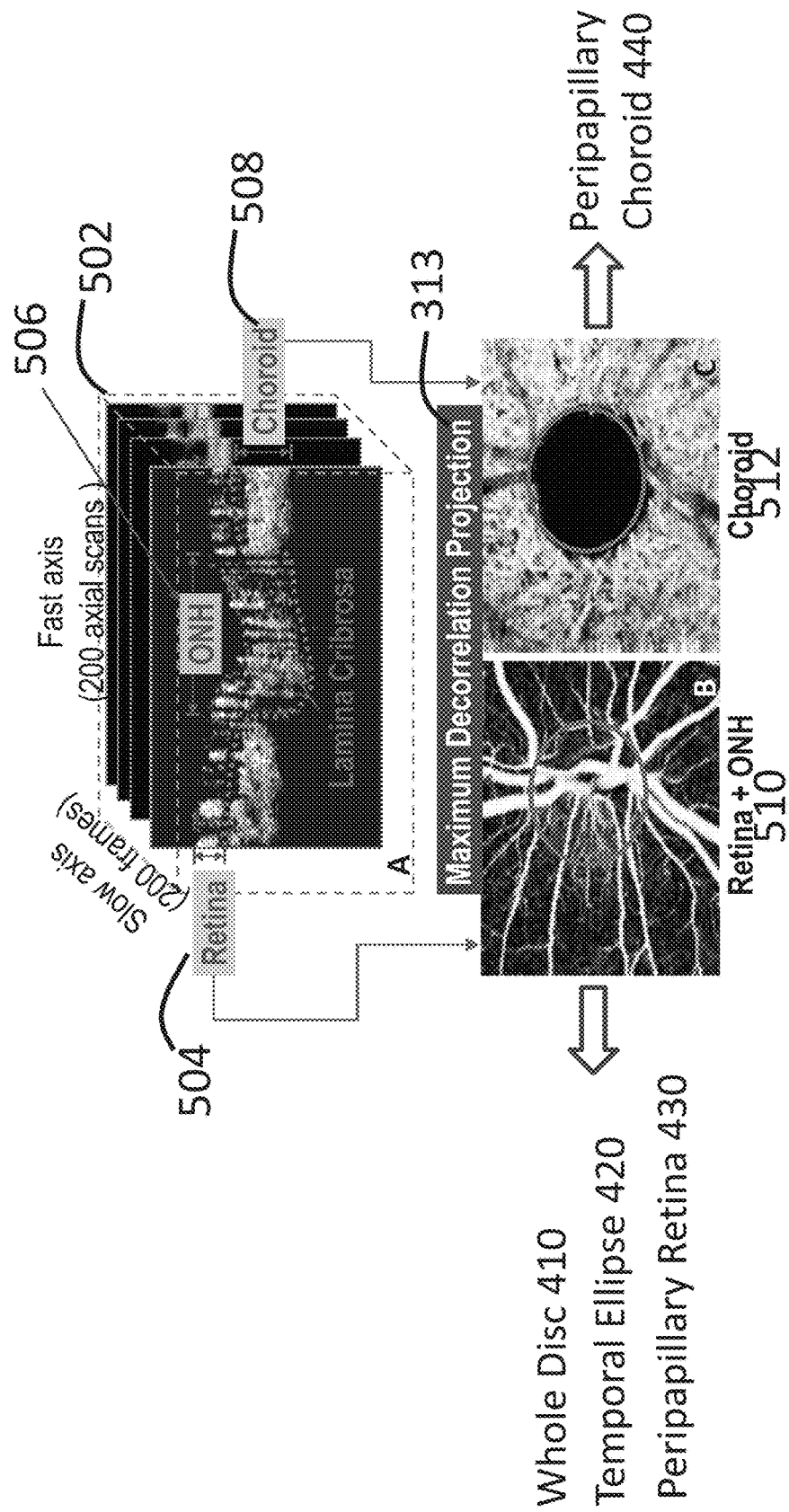
FIG. 22 illustrates an exemplary alternative segmentation method for the ocular nerve head (OHN).

It should be noted that in ONH scans, the IS/OS 431 and the RPE 441 plane can be set by interpolating their depth just outside the disc boundary for segmentation at B-scans. Other alternative segmentation methods for ONH scans can also be used. For example, as shown by FIG. 22, both retina 504 and ONH 506 can be segmented away from choroid 508 through the entire 3D volume 502 and then segment the en face retina and ONH angiography 510 and en face choroid angiography 512 to obtain whole disc 410, temporal ellipse 420 and peripapillary retina 430 and choroid 440. In addition, the choroid of 50 μm can be chosen to better represent the inner choroidal part, choriocapillaris layer [Roh and Weiter, "Retinal and Choroidal Circulation" in *Ophthalmology*, M. Yanoff and J. S. Duker eds. (Mo: Mosby Elsevier, St. Louis, 2008)] and to avoid the effects from the signal voids in the outer choroid [Jia et al., *Opt. Express* 20:47190-4725 (2012)]. Alternatively, choroid thickness can also be slightly changed.

Figure 23:
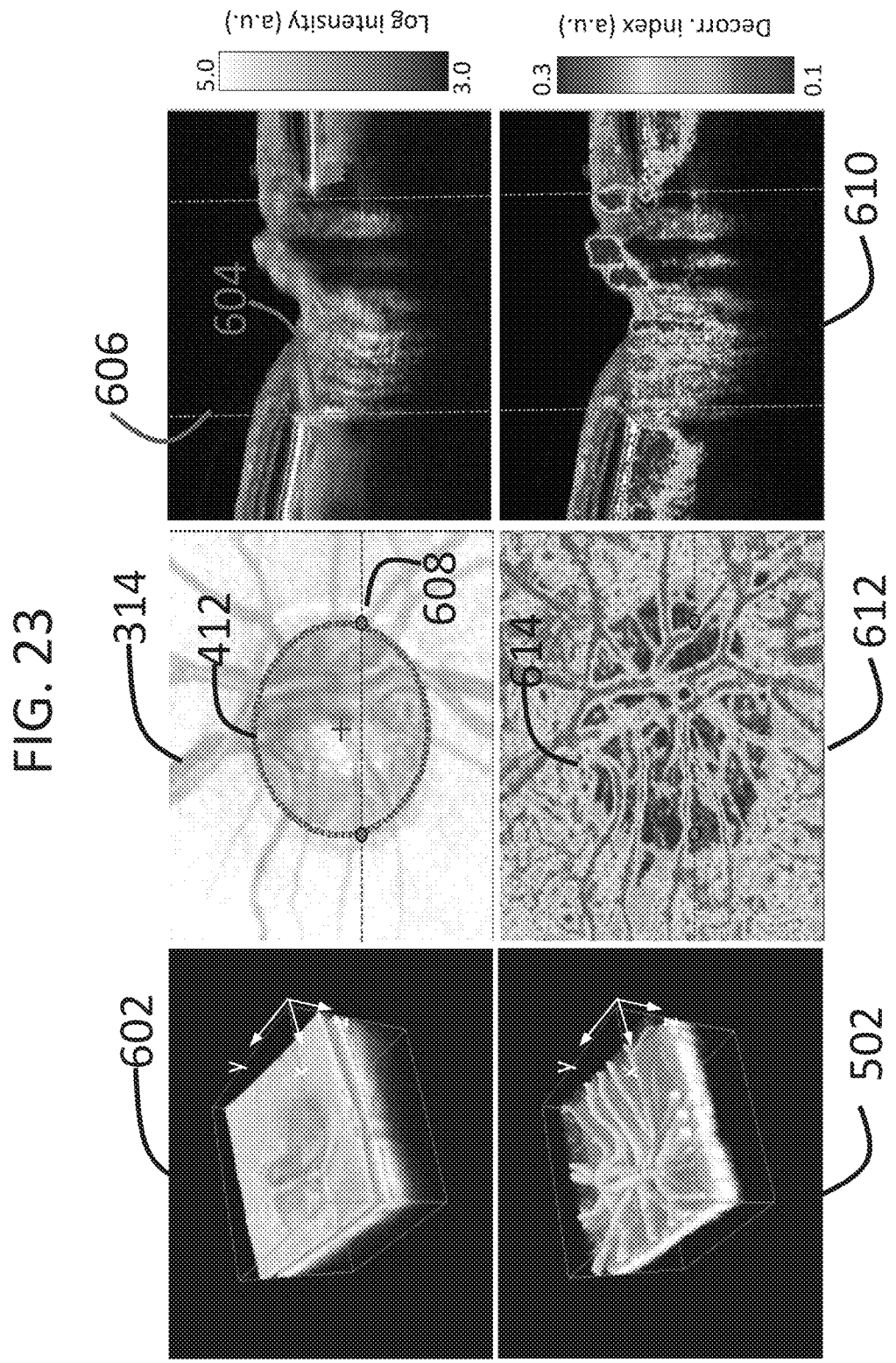
FIG. 23 illustrates an exemplary method for detecting disc margin.

An example demonstrating how to detect optic disc boundary 412 and temporal ellipse of disc 422 is described herein below and in FIG. 23. The NCO 604, which is the termination of the retinal pigment epithelium (RPE)/Bruch's membrane (BM) complex [Strouthidis et al., *Invest. Ophthamol. Vis. Sci.* 50:214-223 (2009) and Hu et al., *Invest. Ophthamol. Vis. Sci.* 51:5708-5717 (2010)], can be used to define the ONH margin 412 [Strouthidis et al., *Invest. Ophthamol. Vis. Sci.* 50:4709-4718 (2009)]. In OCT cross-sectional B-scans, the boundary of the NCO 604, indicated by two green dashed lines 606 is determined by the termination of the RPE/BM complex (two green arrows) 604. It corresponds to the two margin points 608 at the disc region. These representative margin points are transferred on the corresponding flow cross-sectional image 610 and en face projection maps 612. The boundary produced by the surrounding peripapillary choroidal blood flow 614 in the flow data 502 is not optimally used as the detection method for disc margin 412.

Figure 24:
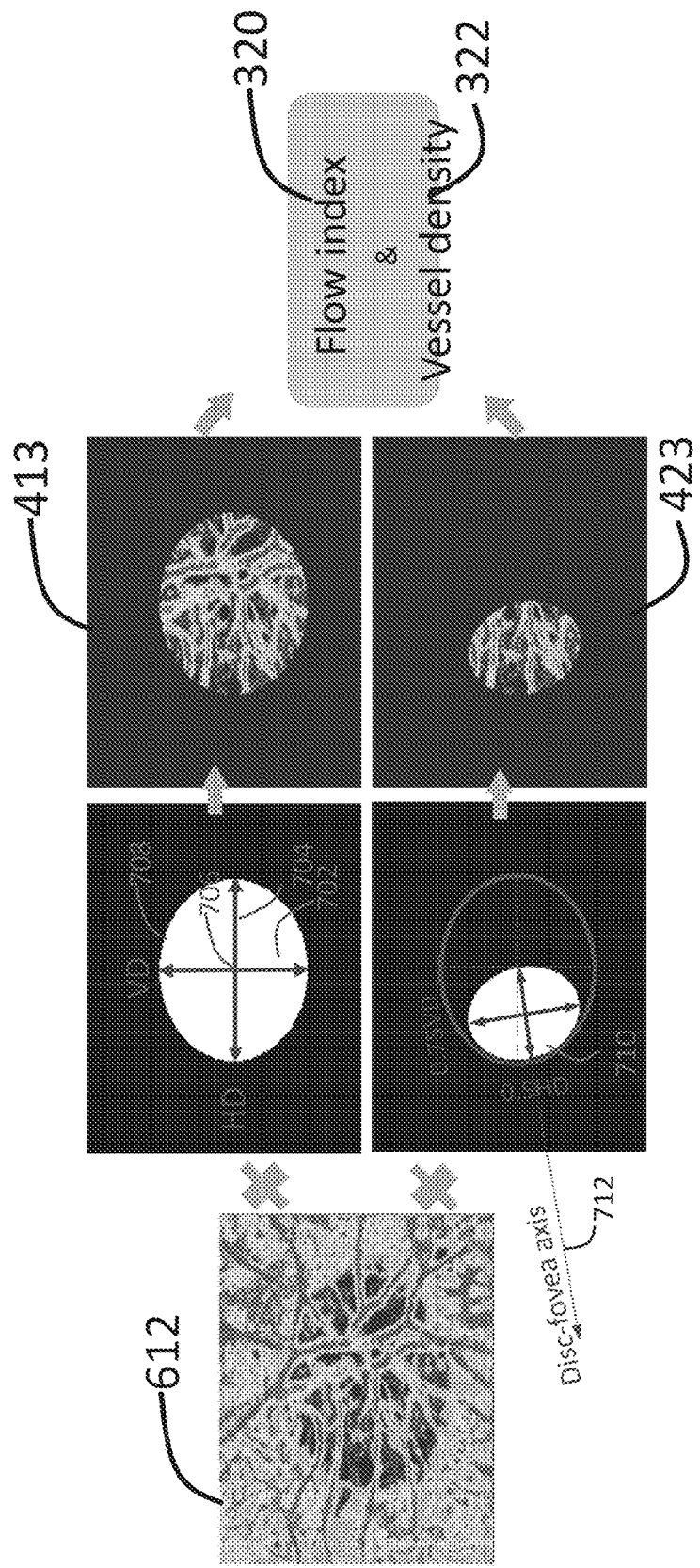
FIG. 24 illustrates an exemplary method for quantifying ONH blood flow.

Because the NCO 604 is detectable, it can be manually delineated on the reflectance projection image 314. Shown by FIG. 24, the major 702 and minor axes 704 of the ellipse are calculated along the vertical and horizontal directions. The approximate center of disc is the centroid of the selected ellipse 706.

After the position and dimensions of a disc are determined, the whole disc 412 and temporal ellipse areas 422 can be segmented for quantitative analysis. The optic disc mask 708 is idealized as an ellipse with vertical diameter (VD) 702 and horizontal diameter (HD) 704. The mask value is 1 inside the ellipse and 0 outside. An elliptical mask 710 is also defined for the disc region temporal to the major superior and inferior branch arteries and veins. The temporal ellipse 422 has a major axis diameter of 0.75 VD and a minor axis diameter of 0.50 HD. The temporal ellipse is tilted inferiorly to fit the tilt of the disc vessel pattern associated with the tilt of the disc-fovea axis 712. According to the literature measurements on the normal population [J. M. McDonnel, "Ocular embryology and anatomy," in *Retina*, S. J. Ryan, ed. (CV Mosby, St Louis, 1989), pp. 5-16], the average value of this angle is 7.1°. The temporal ellipse angiography 423 does not contain any major branch retinal blood vessels and therefore may be a better measure of local disc microcirculation.

Definition and Calculation of Flow Index and Vessel Density

By multiplying different masks 317 with original blood flow projection map 316, respectively, the segmented flow maps 318 can be acquired for further quantification.

The flow index 320 is defined as the average decorrelation values in the segmented area, which can be given by, $$\frac{\int_A D \cdot V dA}{\int_A dA} \quad (V = 1, \text{ if vessel}; V = 0, \text{ if not}) \quad (1)$$

The vessel density is defined as the percentage area occupied by vessels in the segmented area, using the following formula, $$\frac{\int_A V dA}{\int_A dA} \quad (V = 1, \text{ if vessel}; V = 0, \text{ if not}) \quad (2)$$

Where A can be segmented en face flow area 318, D is the decorrelation value acquired by SSADA 303. The threshold used to judge V is 1 or 0 and was set at 0.125, two standard deviations above the mean decorrelation value in noise region. As described by previous report [Jia et al., *Opt. Express* 20:4710-4725 (2012)], the central FAZ 451 in the normal eyes can be chosen as a noise region after the same scanning pattern 100 was applied on the macular region, and then calculated decorrelation values by SSADA 303.

Detection Fovea Avascular Zone and Other Areas of Non-Perfusion

Figure 25:
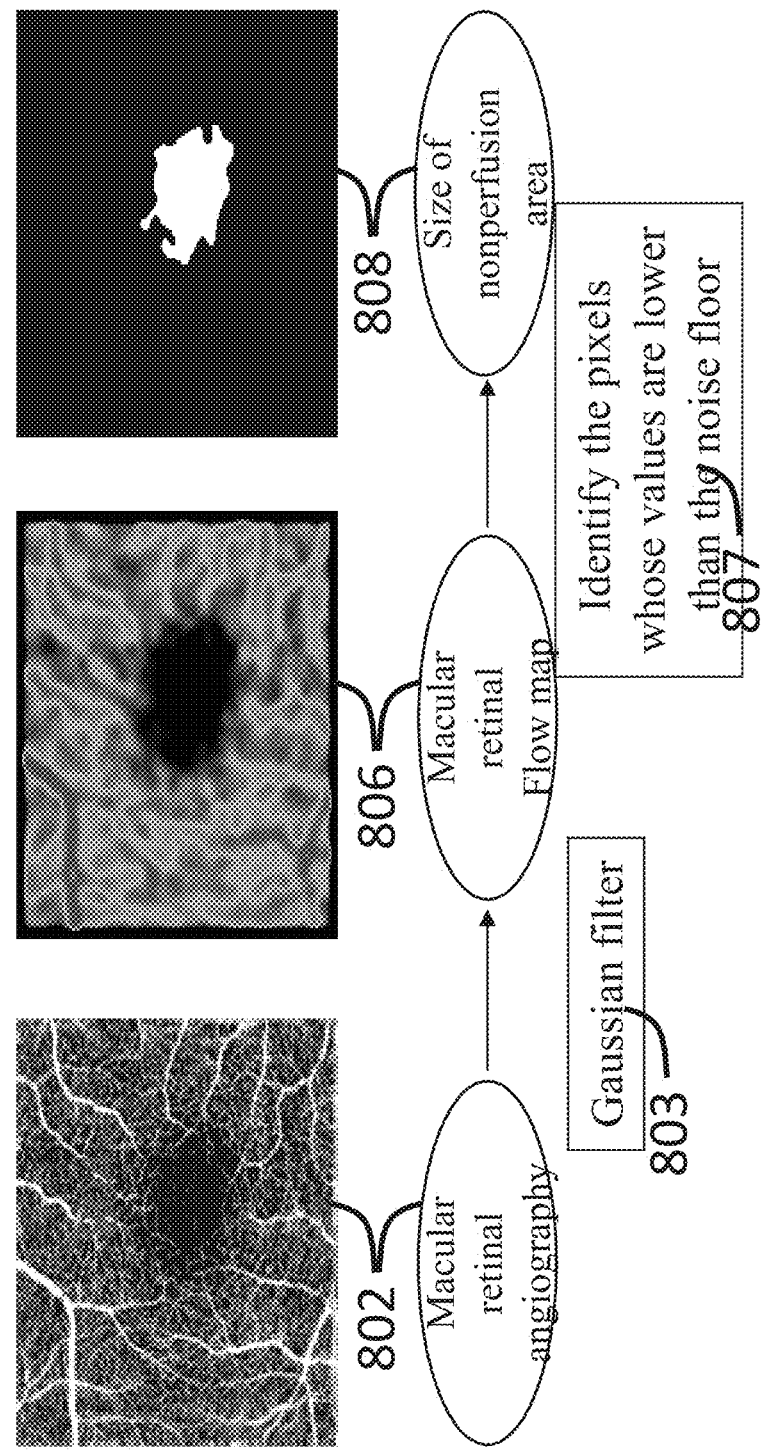
FIG. 25 illustrates detection of the fovea avascular zone and other areas of non-perfusion.

First, a macular retinal angiography 802 of 200×200 pixels, as shown in FIG. 25, is obtained by projecting 3D retinal vasculature 502 segmented between ILM 411 and IS/OS 431. Then this angiography 802 can be smoothed through a Gaussian filter 803. A Gaussian filter 803 is an effective smoothing filter for random noise reduction. In practice, the standard deviation and the window size of a Gaussian filter 803 should be chosen with care to smooth the capillary bed around FAZ 451. Their values are usually chosen based on the diameters of main retinal vessel branches 804. Typically, a σ value of 75 μm is chosen with a window size of 150 μm×150 μm because visually they generate smoothed 2D angiogram 806 for the subsequent analyses. The non-perfusion information 808 can be computed by identifying the pixels whose values are lower than the noise floor 807. In this part, the parameters chosen for Gaussian filter 803 can be varied according to the pixel size.

C. Further Embodiments

Preliminary studies were carried out utilizing the technology described herein. The swept-source OCT system was operated at the center wavelength of 1050 nm, speed of 100,000 axial scans per second, axial resolution of 5 µm and spot diameter of 18 µm (FWHM amplitude). With this configuration and the scan pattern described previously, the B-scan frame rate of the system was 500 frames per second; therefore, 1600 B-scans were acquired to form a 3D data cube, corresponding to an acquisition time of 3.4 seconds.

Figure 26:
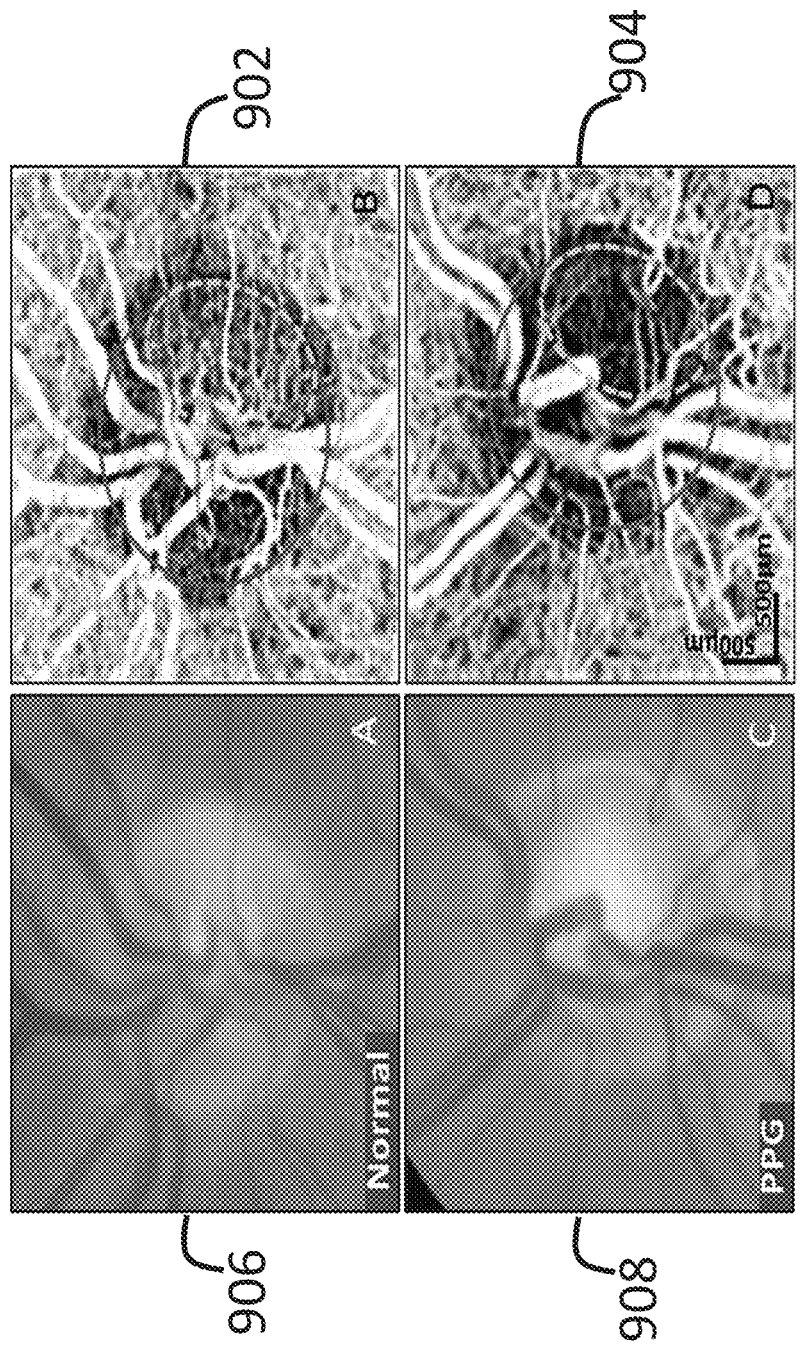
FIG. 26 illustrates OCT angiography showing reduced ONH blood flow in glaucoma.

Both normal and glaucoma groups were studied. Within glaucoma group, two perimetric glaucoma subjects, three pre-perimetric glaucoma subjects and one suspect subjects with ocular hypertension were enrolled for study. In normal subjects, a dense microvascular network was visible on the OCT angiography of the disc 902, in addition to large retinal vessels. This network was visibly attenuated in all PPG subjects, as shown in the disc 904 of FIG. 26. This difference cannot be visualized and quantified by disc photographs normal 906 & PPG 908 respectively. Within the whole disc region, the flow index was reduced by 32% in the glaucoma group. These reductions were statistically significant (see Table 3 below). Regional disc perfusion measurements on the temporal ellipse showed differences between two groups were statistically significant. Thus the estimated reductions were higher than those based on the whole disc region. For this small region quantification, the repeatabilities of the measurements of flow index at whole disc and temporal ellipse were 6.6% and 7.9% respectively. Quantification on peripapillary retina, peripapillary choroid and central macula didn't show any statistical difference between two groups (Table 3).

TABLE 3

Quantification of different vascular beds in glaucoma

| Flow index (dimensionless) | Normal | Glaucoma + Suspect | P-value (Wilcoxon) |
|---|---|---|---|
| ONH - Whole Disc | 0.159 ± 0.020 | 0.108 ± 0.013 | 0.008 |
| ONH - Temporal Ellipse | 0.151 ± 0.014 | 0.072 ± 0.022 | 0.005 |
| Peripapillary Retina | 0.141 ± 0.023 | 0.122 ± 0.024 | 0.191 |
| Peripapillary Choroid | 0.226 ± 0.016 | 0.168 ± 0.071 | 0.105 |
| Macular Retina | 0.120 ± 0.017 | 0.112 ± 0.039 | 0.819 |

In the techniques described herein, the major superior and inferior branches of the retinal vessels on the temporal side were excluded, and quantifications focused mainly on ONH microvascular beds. Preliminary results suggest that in early glaucoma the reduction of ONH microvascular flow is much more dramatic than that of whole ONH circulation. This suggests that quantification performed on microvascular perfusion may be more sensitive for detecting ONH circulatory changes in early glaucoma patients.

For ONH angiography, ONH flow index and peripapillary choroidal flow index are important for the diagnosis and evaluation of glaucoma. Differences between normal and glaucoma in a pilot clinical study were shown. Macular angiography is useful for macular diseases. Perifoveal retinal flow index and macular retinal flow map (size of foveal avascular zone, and identification of any other nonperfusion area) are important for the evaluation of macular ischemia in diabetic retinopathy. Macular choroidal flow index and macular choroidal flow map are important in the evaluation of AMD.

In one embodiment, for the diagnosis of age-related macular degeneration, measuring the flow index of and detecting an impairment in blood flow in either/both of the choroidal neovascular membrane and/or macular choroid is of primary importance. In another embodiment, for the diagnosis of glaucoma, measuring the flow index of and detecting an impairment in blood flow in the ocular nerve head is of primary importance. Finally, in yet an additional embodiment, for the diagnosis of diabetic retinopathy, measuring the flow index of and detecting an impairment in blood flow in the perifoveal avascular region is of primary importance. Data confirming the above described correlations not shown (manuscripts in preparation).

The disclosure set forth above encompasses multiple distinct embodiments. While each of these embodiments have been disclosed in its preferred form, the specific embodiments as disclosed and illustrated herein are not to be considered in a limiting sense as numerous variations are possible. The subject matter of the present disclosure includes all novel and non-obvious combinations and sub-combinations of the various elements, features, functions and/or properties disclosed herein. Similarly, where any claim recites "a" or "a first" element or the equivalent thereof, such claim should be understood to include incorporation of one or more such elements, neither requiring nor excluding two or more such elements.

What is claimed is:

1. A method for measuring in vivo blood flow in a region of a sample to be performed by an optical coherence tomography (OCT) apparatus, the method comprising:
   obtaining digital M-B scans of OCT spectrum for the region, wherein individual M-B scans include multiple B-scans at a same scan location;
   spectrally splitting, after the digital M-B scans are obtained, the M-B scans of OCT spectrum into respective images of a plurality of spectral bands of the OCT spectrum;
   obtaining a flow image from decorrelation values of the M-B scans in the plurality of spectral bands;
   obtaining a reflectance intensity image from the M-B scans of OCT spectrum;
   identifying one or more landmarks in the reflectance intensity image;
   segmenting the flow image based on the identified one or more landmarks to obtain a segmented flow image; and
   determining a flow index and a vessel density for the region of the sample based on the segmented flow image.

2. The method of claim 1, further comprising:
   obtaining an en face reflectance image from the reflectance intensity image;
   obtaining an en face segmented flow image from the segmented flow image;
   identifying one or more landmarks on the en face reflectance image; and
   segmenting the en face segmented flow image based on the one or more landmarks identified on the en face reflectance image to generate a segmented en face flow image;

wherein determining the flow index and the vessel density based on the segmented flow image includes determining the flow index and the vessel density based on the segmented en face flow image.

3. The method of claim 2, wherein:
obtaining the en face reflectance image includes identifying a maximum reflectance of the reflectance intensity image at respective transverse positions of the reflectance intensity image; and
obtaining the en face segmented flow image includes identifying a maximum decorrelation value of the segmented flow image at respective transverse positions of the segmented flow image.

4. The method of claim 2, wherein determining the flow index is performed according to:

$$\frac{\int_A D \times V dA}{\int_A dA}$$

wherein D corresponds to the decorrelation values from the flow image, A corresponds to an area of the segmented en face flow image, and V has a value of 1 if a respective location of the area is determined to have a vessel and a value of 0 if the respective location of the area is determined not to have a vessel.

5. The method of claim 2, wherein determining the vessel density is performed according to:

$$\frac{\int_A V dA}{\int_A dA}$$

wherein A corresponds to an area of the segmented en face flow image, and V has a value of 1 if a respective location of the area is determined to have a vessel and a value of 0 if the respective location of the area is determined not to have a vessel.

6. The method of claim 1, wherein the one or more landmarks include an internal limiting membrane (ILM), a neural canal opening (NCO), an inner-segment/outer-segment (IS/OS) junction, a retinal pigment epithelium (RPE), or a fovea avascular zone (FAZ).

7. The method of claim 1, wherein segmenting the flow image is performed using an elliptical mask oriented with respect to the identified one or more landmarks to obtain the segmented flow image.

8. The method of claim 1, wherein the flow index corresponds to an average decorrelation value in a segmented area of the segmented flow image.

9. The method of claim 1, wherein the vessel density corresponds to a percentage of a segmented area of the segmented flow image that is occupied by vessels.

10. The method of claim 1, further comprising determining a total retinal blood flow based on the flow index and the vessel density.

11. The method of claim 1, further comprising determining a volumetric blood flow rate based on the flow index and the vessel density.

12. The method of claim 1, wherein the flow image is an OCT angiogram.

13. A system for quantitatively measuring blood flow in an in vivo sample, the system comprising:
an optical coherence tomography (OCT) apparatus to perform M-B scans of OCT spectrum on the in vivo sample, wherein individual M-B scans include multiple B-scans at a same scan location; and
one or more processors coupled to the OCT apparatus and adapted to cause the OCT apparatus to:
obtain a flow image from the M-B scans using a split-spectrum amplitude-decorrelation angiography (SSADA) imaging process, the flow image including decorrelation values determined from the M-B scans for a plurality of spectral bands;
obtain a reflectance intensity image from the M-B scans of OCT spectrum;
identify one or more landmarks in the reflectance intensity image;
segment the flow image based on the identified one or more landmarks to obtain a segmented flow image; and
determine a flow index and a vessel density for the in vivo sample based on the segmented flow image.

14. The system of claim 13, wherein the one or more processors are further adapted to cause the OCT apparatus to:
obtain an en face reflectance image from the reflectance intensity image;
obtain an en face segmented flow image from the segmented flow image;
identify one or more landmarks on the en face reflectance image; and
segment the en face segmented flow image based on the one or more landmarks identified on the en face reflectance image to generate a segmented en face flow image;
wherein, to determine the flow index and the vessel density based on the segmented flow image, the OCT apparatus is to determine the flow index and the vessel density based on the segmented en face flow image.

15. The system of claim 14, wherein:
to obtain the en face reflectance image, the OCT apparatus is to identify a maximum reflectance of the reflectance intensity image at respective transverse positions of the reflectance intensity image; and
to obtain the en face segmented flow image, the OCT apparatus is to identify a maximum decorrelation value of the segmented flow image at respective transverse positions of the segmented flow image.

16. The system of claim 14, wherein the flow index is determined according to:

$$\frac{\int_A D \times V dA}{\int_A dA}$$

wherein D corresponds to the decorrelation values from the flow image, A corresponds to an area of the segmented en face flow image, and V has a value of 1 if a respective location of the area is determined to have a vessel and a value of 0 if the respective location of the area is determined not to have a vessel.

17. The system of claim 14, wherein the vessel density is determined according to:

$$\frac{\int_A V dA}{\int_A dA}$$

wherein A corresponds to an area of the segmented en face flow image, and V has a value of 1 if a respective location of the area is determined to have a vessel and a value of 0 if the respective location of the area is determined not to have a vessel.

18. The system of claim 13, wherein the one or more landmarks include an internal limiting membrane (ILM), a neural canal opening (NCO), an inner-segment/outer-segment (IS/OS) junction, a retinal pigment epithelium (RPE), or a fovea avascular zone (FAZ).

19. The system of claim 13, wherein the flow image is segmented using an elliptical mask oriented with respect to the identified one or more landmarks to obtain the segmented flow image.

20. The system of claim 13, wherein the flow index corresponds to an average decorrelation value in a segmented area of the segmented flow image.

21. The system of claim 13, wherein the vessel density corresponds to a percentage of a segmented area of the segmented flow image that is occupied by vessels.

22. The system of claim 13, wherein the one or more processors are further adapted to cause the OCT apparatus to determine a total retinal blood flow based on the flow index and the vessel density.

23. The system of claim 13, wherein the one or more processors are further adapted to cause the OCT apparatus to determine a volumetric blood flow rate based on the flow index and the vessel density.

24. The system of claim 13, wherein the flow image is an OCT angiogram.

* * * * *

UNITED STATES PATENT AND TRADEMARK OFFICE
CERTIFICATE OF CORRECTION

| | | |
|---|---|---|
| PATENT NO. | : 10,485,423 B2 | Page 1 of 1 |
| APPLICATION NO. | : 15/219046 | |
| DATED | : November 26, 2019 | |
| INVENTOR(S) | : Huang et al. | |

It is certified that error appears in the above-identified patent and that said Letters Patent is hereby corrected as shown below:

In the Specification

Column 1; Line 24, under heading ACKNOWLEDGMENT OF GOVERNMENT SUPPORT please replace with "This invention was made with government support under EY013516 awarded by the National Institutes of Health. The government has certain rights in the invention."

Signed and Sealed this
First Day of June, 2021

Drew Hirshfeld
*Performing the Functions and Duties of the*
*Under Secretary of Commerce for Intellectual Property and*
*Director of the United States Patent and Trademark Office*